United States Patent [19]

Daniel et al.

[11] Patent Number: 5,980,455
[45] Date of Patent: Nov. 9, 1999

[54] METHOD FOR MANIPULATING A TISSUE STRUCTURE WITHIN A THORACIC CAVITY

[75] Inventors: S. Christopher Daniel, San Francisco; Robert K. Deckman, San Mateo; Michi E. Garrison, Half Moon Bay, all of Calif.

[73] Assignee: Heartport, Inc., Redwood City, Calif.

[21] Appl. No.: 08/893,066

[22] Filed: Jul. 15, 1997

Related U.S. Application Data

[60] Continuation-in-part of application No. 08/577,547, Dec. 22, 1995, which is a division of application No. 08/294,454, Aug. 23, 1994, Pat. No. 5,613,937, which is a continuation-in-part of application No. 08/163,241, Dec. 6, 1993, Pat. No. 5,571,215, which is a continuation-in-part of application No. 08/023,778, Feb. 22, 1993, Pat. No. 5,452,733.

[51] Int. Cl.$^6$ ..................................................... A61B 1/313
[52] U.S. Cl. ............................ 600/235; 600/227; 600/201
[58] Field of Search ...................................... 600/201, 204, 600/210, 213, 226, 227, 228, 229, 230, 231, 232, 233, 234, 235, 215, 114; 604/49, 142; 606/46; 623/2

[56] References Cited

U.S. PATENT DOCUMENTS

| | | |
|---|---|---|
| 4,122,844 | 10/1978 | Rabban . |
| 4,254,763 | 3/1981 | McCready et al. ................ 600/231 X |
| 5,127,393 | 7/1992 | McFarlin et al. . |
| 5,167,223 | 12/1992 | Koros et al. . |
| 5,174,278 | 12/1992 | Babkow . |
| 5,231,974 | 8/1993 | Giglio et al. . |
| 5,304,183 | 4/1994 | Gourlay et al. . |
| 5,391,156 | 2/1995 | Hildwein et al. . |
| 5,441,042 | 8/1995 | Putnam . |
| 5,441,059 | 8/1995 | Dannan . |
| 5,452,733 | 9/1995 | Sterman et al. . |
| 5,540,648 | 7/1996 | Yoon ........................................ 600/114 |
| 5,613,937 | 3/1997 | Garrison et al. . |
| 5,728,047 | 3/1998 | Edoga ..................................... 600/227 |
| 5,807,243 | 9/1998 | Vierra et al. ........................ 600/235 X |

FOREIGN PATENT DOCUMENTS

| | | |
|---|---|---|
| WO 93/09709 | 5/1993 | WIPO . |
| WO 93/09720 | 5/1993 | WIPO . |
| WO 95/15715 | 6/1995 | WIPO . |

OTHER PUBLICATIONS

Scanlan International, Inc., Surgical Instrumentation Catalog, 1992, p. 81.
Pilling Co., Surgical Instruments Catalog, 1993, pp. 294–296.
Omnitract Surgical Catalog, "Laparoscopic Surgery Instrumentation," pp. 14–16.
Carter, M.G. "A New Retractor For Open Mitral Valve Surgery," *Journal of Thoracic and Cardiovascular Surgery*, 1962, vol. 44, No. 2.

*Primary Examiner*—John P. Leubecker
*Attorney, Agent, or Firm*—Jeffry J. Grainger; Jens E. Hoekendijk

[57] ABSTRACT

A method for manipulating a tissue structure within a body cavity provides for retracting and supporting the heart wall to provide access into the heart during a cardiac surgical procedure. In one embodiment of the present invention, a surgical tool support apparatus comprises a base having an atraumatic tissue-engaging surface and an aperture for receiving an elongate tool. The apparatus also has a clamp assembly aligned with the aperture and spaced-apart from a surface of the base opposite to the tissue-engaging surface. The apparatus is particularly useful in maintaining a retracting force on a surgical tool used to manipulate tissue within a body cavity such as the thoracic cavity.

13 Claims, 16 Drawing Sheets

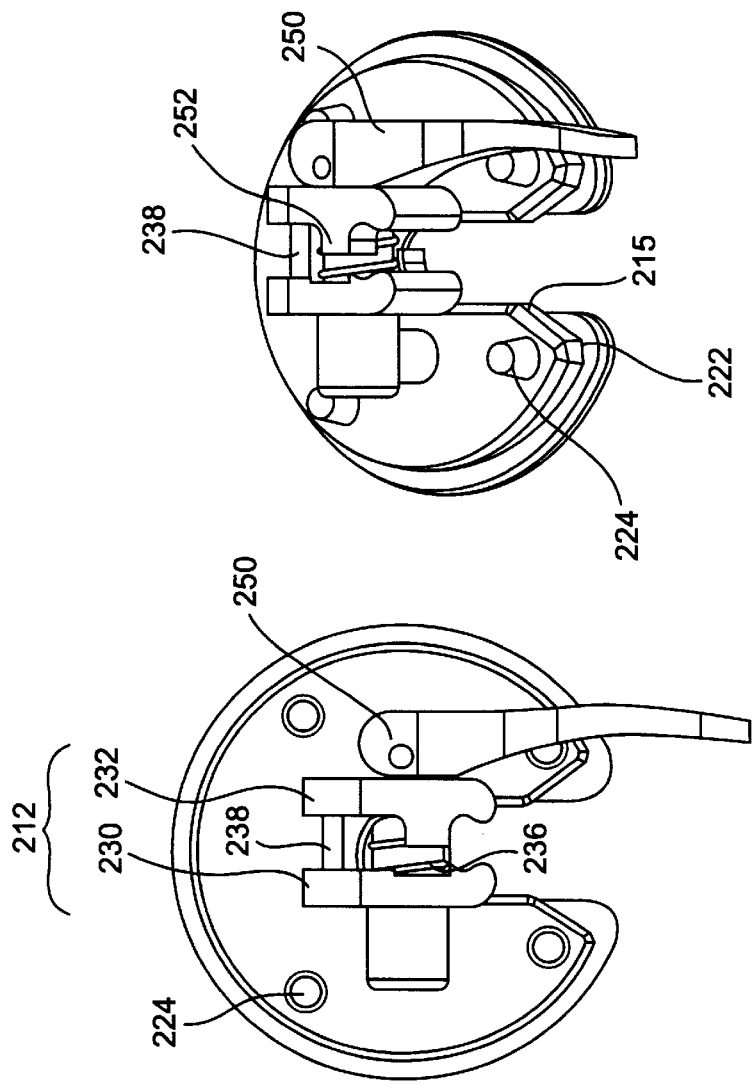
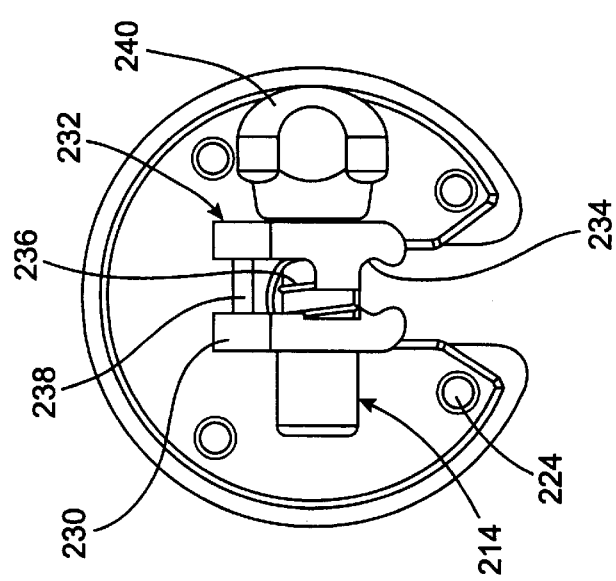
FIG. 6C
FIG. 6B
FIG. 6A

METHOD FOR MANIPULATING A TISSUE STRUCTURE WITHIN A THORACIC CAVITY

CROSS-REFERENCE TO RELATED APPLICATIONS

This application is a continuation-in-part of commonly-assigned, co-pending application Ser. No. 08/577,547, filed Dec. 22, 1995 which is a divisional of 08/294,454, filed Aug. 23, 1994, now U.S. Pat. No. 5,613,937, which is a continuation-in-part of application Ser. No. 08/163,241, filed Dec. 6, 1993 now U.S. Pat. No. 5,571,215, which is a continuation-in-part of application Ser. No. 08/023,778, filed Feb. 22, 1993 now U.S. Pat. No. 5,452,733. The complete disclosures of these applications and patents are hereby incorporated herein by reference.

BACKGROUND OF THE INVENTION

This invention relates generally to instruments and techniques for performing less-invasive surgical procedures, and more specifically, to less-invasive instruments and techniques for retracting tissue structures within body cavities such as the abdomen or thorax.

Various types of surgical procedures are currently performed to investigate, diagnose, and treat diseases of the heart and the great vessels of the thorax. Such procedures include repair and replacement of mitral, aortic, and other heart valves, repair of atrial and ventricular septal defects, pulmonary thrombectomy, treatment of aneurysms, electrophysiological mapping and ablation of the myocardium, and other procedures in which interventional devices are introduced into the interior of the heart or a great vessel.

Using current techniques, many of these procedures require a gross thoracotomy, usually in the form of a median sternotomy, to gain access into the patient's thoracic cavity. A saw or other cutting instrument is used to cut the sternum longitudinally, allowing two opposing halves of the anterior or ventral portion of the rib cage to be spread apart. A large opening into the thoracic cavity is thus created, through which the surgical team may directly visualize and operate upon the heart and other thoracic contents.

Surgical intervention within the heart generally requires isolation of the heart and coronary blood vessels from the remainder of the arterial system, and arrest of cardiac function. Usually, the heart is isolated from the arterial system by introducing an external aortic cross-clamp through a sternotomy and applying it to the aorta between the brachiocephalic artery and the coronary ostia. Cardioplegic fluid is then injected into the coronary arteries, either directly into the coronary ostia or through a puncture in the aortic root, so as to arrest cardiac function. In some cases, cardioplegic fluid is injected into the coronary sinus for retrograde perfusion of the myocardium. The patient is placed on cardiopulmonary bypass to maintain peripheral circulation of oxygenated blood.

Of particular interest to the present invention are intracardiac procedures for surgical treatment of heart valves, especially the mitral and aortic valves. According to recent estimates, more than 79,000 patients are diagnosed with aortic and mitral valve disease in U.S. hospitals each year. More than 49,000 mitral valve or aortic valve replacement procedures are performed annually in the U.S., along with a significant number of heart valve repair procedures.

Various surgical techniques may be used to repair a diseased or damaged valve, including annuloplasty (contracting the valve annulus), quadrangular resection (narrowing the valve leaflets), commissurotomy (cutting the valve commissures to separate the valve leaflets), shortening mitral or tricuspid valve chordae tendonae, reattachment of severed mitral or tricuspid valve chordae tendonae or papillary muscle tissue, and decalcification of valve and annulus tissue. Alternatively, the valve may be replaced, by excising the valve leaflets of the natural valve, and securing a replacement valve in the valve position, usually by suturing the replacement valve to the natural valve annulus. Various types of replacement valves are in current use, including mechanical and biological prostheses, homografts, and allografts, as described in Bodnar and Frater, *Replacement Cardiac Valves* 1–357 (1991), which is incorporated herein by reference. A comprehensive discussion of heart valve diseases and the surgical treatment thereof is found in Kirklin and Barratt-Boyes, *Cardiac Surgery* 323–459 (1986), the complete disclosure of which is incorporated herein by reference.

The mitral valve, located between the left atrium and left ventricle of the heart, is most easily reached through the wall of the left atrium, which normally resides on the posterior side of the heart, opposite the side of the heart that is exposed by a median sternotomy. Therefore, to access the mitral valve via a sternotomy, the heart is rotated to bring the left atrium into an anterior position accessible through the sternotomy. An opening, or atriotomy, is then made in the right side of the left atrium, anterior to the right pulmonary veins. The atriotomy is retracted by means of sutures or retraction devices, exposing the mitral valve directly posterior to the atriotomy. One of the aforementioned techniques may then be used to repair or replace the valve.

An alternative technique for mitral valve access may be used when a median sternotomy and/or rotational manipulation of the heart are undesirable. In this technique, a large incision is made in the right lateral side of the chest, usually in the region of the fourth intercostal space. One or more ribs may be removed from the patient, and other ribs near the incision are retracted outward to create a large opening into the thoracic cavity. The left atrium is then exposed on the posterior side of the heart, and an atriotomy is formed in the wall of the left atrium, through which the mitral valve may be accessed for repair or replacement.

Using such open-chest techniques, the large opening provided by a median sternotomy or right thoracotomy enables the surgeon to see the mitral valve directly through the left atriotomy, and to position his or her hands within the thoracic cavity in close proximity to the exterior of the heart for manipulation of surgical instruments, removal of excised tissue, and/or introduction of a replacement valve through the atriotomy for attachment within the heart. However, these invasive, open-chest procedures produce a high degree of trauma, a significant risk of complications, an extended hospital stay, and a painful recovery period for the patient. Moreover, while heart valve surgery produces beneficial results for many patients, numerous others who might benefit from such surgery are unable or unwilling to undergo the trauma and risks of current techniques.

In response to the various problems associated with open-chest procedures, new methods of performing closed-chest surgery on the heart using minimally invasive thoracoscopic techniques have been recently developed. In these methods, the patient's heart is arrested by occluding the patient's aorta between the coronary arteries and the brachiocephalic artery with an expandable balloon on the distal end of an endovascular catheter introduced via a femoral artery. Cardioplegic fluid is then delivered to the patient's myocardium through a lumen in the same catheter or through a catheter positioned in the coronary sinus via a peripheral vein. To repair or replace the mitral valve, minimally-invasive cutting and suturing instruments are then introduced thoracoscopically through a trocar sleeve in the right lateral portion of the chest. A complete description of such methods is found in commonly assigned, co-pending application Ser. No. 08/163,241, filed Dec. 6, 1993, now U.S. Pat. No. 5,571,215 which has been previously incorporated herein by reference.

This new generation of thoracoscopic methods of performing heart valve repair has, of course, created many new challenges. One such challenge is that of retracting the left atrial wall to open the atriotomy so that the mitral valve can be exposed for the surgical procedure. The heart wall must be retracted anteriorly to suitably expose the mitral valve and provide access through the atriotomy for the cutting and suturing instruments introduced through the right lateral portion of the chest. In addition, the instruments that retract the heart wall must be introduced in a minimally-invasive manner through small percutaneous incisions or cannulae positioned in intercostal spaces in the patient's rib cage.

Introducing an instrument through an intercostal space in the anterior side of the chest presents additional problems. One such problem is that the patient's rib cage is typically structured so that the ribs in the anterior portion of the chest are closer together than in the lateral portions of the chest. In addition, the tissue layer in the anterior chest wall contains nerves that could be damaged by a large percutaneous incision. Therefore, a retraction device introduced from the anterior side should be as small as possible, preferably on the order of 3–8 mm, to fit within the smaller anterior intercostal spaces and to avoid unnecessary trauma to the patient. Another problem is that the part of the retraction device that engages the heart wall must be wide enough to engage a sufficient portion of the heart wall to open the atriotomy enough to expose the mitral valve. It must also be long enough to extend a sufficient distance into the heart to extend beneath the interatrial septum and prevent it from sagging or otherwise inhibiting access to the mitral valve. Introducing an instrument which is large enough to sufficiently expose the mitral valve through the smaller intercostal spaces in the anterior portion of the chest is problematic.

Additionally, portions of the heart wall are typically retracted for a substantial period of time during the mitral valve replacement procedure. Conventionally, retraction is maintained by a nurse or surgeon physically holding a retractor in position for the duration of time required. Alternatively, some surgeons have jerry-rigged scissor clamps or other devices to hold the retractor in position during surgery. The first approach is an inefficient use of resources, and the second creates a dangerous situation should one of the jury-rigged clamps fail. These approaches also fail to provide a reliable and consistently stable retraction of heart tissue as required during such delicate interventional procedures. Although some large, floor-based positioning devices exist that have an arm extending from the floor up and over the patient, they fail to provide the ease of removal and compact configuration required in the close quarters of the operating area. The larger devices tend to retract laterally when the device cannot be positioned directly over the site of retraction and are difficult to remove if fluoroscopy or other diagnostic procedures need to be performed during the course of valve replacement.

What is needed, therefore, are improved apparatus, systems, and methods for manipulating a tissue structure in a body cavity via a small percutaneous penetration or cannula. Particularly, the apparatus, systems, and methods should be capable of providing constant and reliable retraction of tissue in the thoracic cavity during delicate and sensitive procedures such as mitral valve replacement. The apparatus would preferably be of compact design, being easily deployable, adjustable, and removable from the patient, while providing constant, reliable retraction without requiring the services of a nurse or doctor to maintain retracting force.

SUMMARY OF THE INVENTION

The present invention provides apparatus, systems, and methods for manipulating a tissue structure in a body cavity through a small percutaneous penetration in a patient. The system is preferably configured for use with a small percutaneous penetration into a body cavity and for retracting an incision in the left atrium from the anterior side of the chest. The system is well suited for providing constant and reliable retraction of the heart wall, making the invention particularly useful during surgeries such as mitral valve replacement. While being especially useful for thoracoscopy, the present invention is also useful in other surgical procedures, such as laparoscopy and pelviscopy.

According to the present invention, a method for manipulating tissue structure within the thoracic cavity of a patient comprises the step of introducing a tissue positioning tool having a shaft into the thoracic cavity through a percutaneous penetration. A force is applied to the shaft to engage the tissue structure with the tissue positioning tool, so as to reposition the tissue structure within the thoracic cavity. A tool support apparatus is positioned on an outer surface of the thoracic cavity. The positioning of the tool support apparatus may occur prior to or after the introduction of the tool into the cavity. With the desired force applied to the shaft, the shaft of the tissue positioning tool is fixedly secured to the support apparatus. The force to the shaft is maintained against the repositioned tissue structure through contact of the tool support apparatus against an outer surface of the thoracic cavity.

In one embodiment of the present invention, the method comprises a positioning step where a base of the support apparatus is rested tangentially on the outer surface of the thoracic cavity. To facilitate engagement of the apparatus with the shaft of the positioning tool, a clamp assembly of the support apparatus is aligned with a longitudinal axis of the shaft. The base is preferably positioned so that an aperture in the base rests directly over the percutaneous penetration. This allows the support apparatus to provide retraction in a direction normal to the outer surface of the cavity. It should be understood, however, that the support apparatus can provide retraction at a variety of different angles and is not limited to retraction at angles perpendicular to the surface of the cavity.

In another embodiment of the present invention, the introduction step of the method comprises introducing a tissue supporting member having a contact surface into the thoracic cavity through a first percutaneous penetration. The shaft of the tool, having a longitudinal axis, is introduced through a second percutaneous penetration. The tissue supporting member is connected to the shaft within the thoracic cavity to form a tissue positioning tool. Assembling the tool within the thoracic cavity allows the use of positioning devices having parts and surfaces too large to be introduced through the typically smaller penetration from which the shaft of the tool extends.

According to the present invention, a surgical tool support apparatus comprises a base having an atraumatic tissue-engaging surface and an aperture for receiving an elongate tool. The apparatus also has a clamp assembly aligned with the aperture and spaced-apart from a surface of the base opposite to the tissue-engaging surface.

In one embodiment of the invention, the apparatus comprises a base having a rigid plate and a biocompatible elastomeric cushion over the atraumatic surface for minimizing pressure trauma to the patient. The cushion may be removably attached to the rigid plate. Having the cushion and other parts of the invention removable from each other facilitates cleaning and replacement of the parts of the apparatus.

In another embodiment of the invention, the clamp assembly of the apparatus is rotatably attached to the base about an axis generally parallel to the atraumatic tissue-engaging surface. The clamp assembly typically comprises a pair of jaws where at least one of the jaws has a flange extending from a surface of the jaw to facilitate alignment when the jaws close. The clamp assembly also has a closing mechanism for bring the pair of jaws into contact.

According to the present invention, a system for manipulating tissue structure within the thoracic cavity comprises a linking member, a first clamp, and a second clamp. The first clamp has a first jaw and a second jaw where the first jaw is movably coupled to the second jaw by the linking member. The second clamp is mounted on the second jaw of the first clamp for fixedly engaging the linking member. The second clamp is preferably has a rotational linkage for rotatably coupling the second jaw to the linking member.

In a further aspect of the present invention, a kit of the present invention comprises a base having an atraumatic tissue-engaging surface and an aperture for receiving an elongate tool. The kit also has a clamp assembly aligned with the aperture and spaced-apart from a surface of the base opposite to the tissue-engaging surface. Instructions for use setting forth a method of the present invention are enclosed in a package along with the base and the clamp assembly. A retractor or tissue positioning tool may also be included in the package.

It should be understood that while the invention is described in the context of thoracoscopic surgery on the left atrium and mitral valve, the systems and methods disclosed herein are equally useful on other types of tissue structures and in other types of surgery, such as laparoscopy and pelviscopy.

A further understanding of the nature and advantages of the invention may be realized by reference to the remaining portions of the specification and the drawings.

BRIEF DESCRIPTION OF THE DRAWINGS

FIGS. 6A–6C are overhead perspective views of the apparatus of FIG. 5A fitted with a variety of clamp assembly closure devices;

DETAILED DESCRIPTION OF SPECIFIC EMBODIMENTS

I. Introduction

The invention provides methods and devices for facilitating surgical interventions within body cavities such as the thoracic cavity. While the specific embodiments of the invention described herein will refer to mitral valve repair and replacement, it should be understood that the invention will be useful in performing retraction for a great variety of surgical procedures, including repair and replacement of aortic, tricuspid, or pulmonary valves, repair of atrial and ventricular septal defects, pulmonary thrombectomy, removal of atrial myxoma, patent foramen ovale closure, treatment of aneurysms, electrophysiological mapping and ablation of the myocardium, myocardial drilling, coronary artery bypass grafting, angioplasty, atherectomy, correction of congenital defects, and other procedures in which interventional devices are introduced into the interior of body cavities such as the thoracic cavity.

The present invention is of particular use in minimally invasive procedures performed in the chest through percutaneous intercostal penetrations. The terms "percutaneous intercostal penetration" and "intercostal penetration" as used herein refer to a penetration, in the form or a small cut, incision, hole, cannula, trocar sleeve, or the like, through the chest wall between two adjacent ribs, wherein the patient's rib cage and sternum remain substantially intact, without cutting, removing, or significantly displacing the ribs or sternum. These terms are intended to distinguish a gross thoracotomy such as a median sternotomy, wherein the sternum and/or one or more ribs are cut or removed from the rib cage, or one or more ribs are retracted significantly, to create a large opening into the thoracic cavity. A "percutaneous intercostal penetration" may abut or overlap the adjacent ribs between which it is formed, but the maximum width of the penetration which is available for introduction of instruments, prostheses and the like into the thoracic cavity will be the width of the intercostal space, bounded by two adjacent ribs in their natural, substantially undeflected positions. It should be understood that one or more ribs may be retracted or deflected a small amount without departing from the scope of the invention; however, the invention specifically seeks to avoid the pain, trauma, and complications which result from the large deflection or cutting of the ribs in conventional, open-chest techniques.

Advantageously, the present invention facilitates the performance of procedures using percutaneous penetrations within intercostal spaces of the rib cage to obviate the need for a median sternotomy or other form of gross thoracotomy. The present invention is of particular use in closed-chest mitral valve replacement.

II. Overview of a Closed-Chest Mitral Valve Replacement

Figure 1:
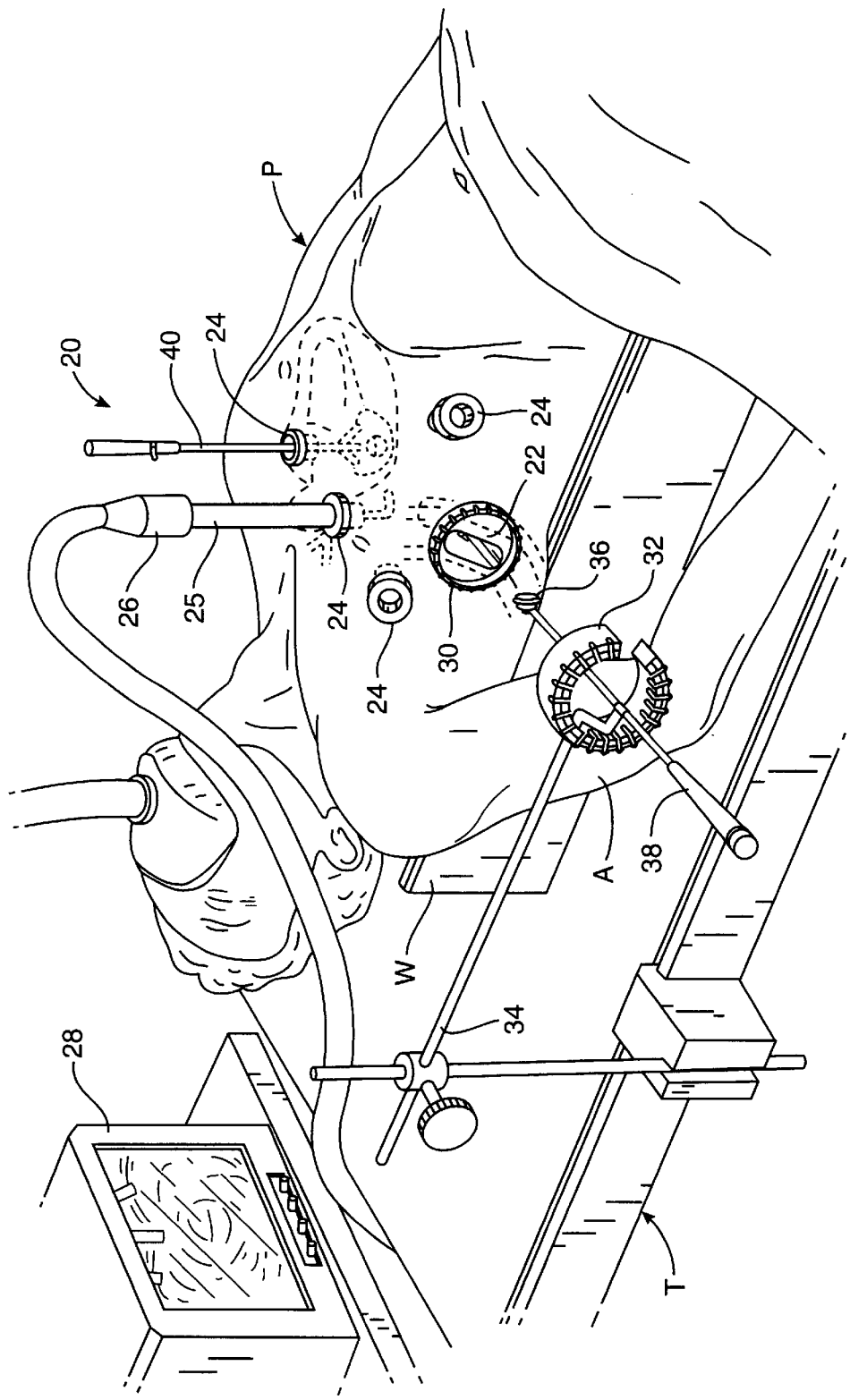
FIG. 1 is a perspective view of a closed-chest mitral valve replacement using minimally invasive techniques and a retractor.

A method for performing closed-chest mitral valve replacement will be described with reference to FIGS. 1–10. FIG. 1 illustrates a system 20 for closed-chest valve replacement positioned in a patient P on an operating table T. Preferably, a wedge or block W having a top surface angled at approximately 20° to 45° is positioned under the right side of patient P so that the right side of the patient's body is somewhat higher than the left side. The patient's right arm A is allowed to rotate downward to rest on table T, exposing the right lateral side of the patient's chest.

The valve replacement system 20 includes an access cannula 22 positioned percutaneously within an intercostal space between two ribs (shown in phantom) in a right lateral side of the patient's chest. Additional thoracoscopic trocar sleeves 24 of conventional construction are positioned within intercostal spaces in the right lateral chest inferior and superior to access cannula 22, as well as in the right anterior (or ventral) portion of the chest. An endoscope 25 of conventional construction is positioned through a percutaneous intercostal penetration into the patient's chest, usually through one of trocar sleeves 24. The distal end of endoscope 25 (shown in phantom) is preferably configured to view at an angle between about 30° and 90° relative to the shaft of endoscope 25, to facilitate visualization of the heart from the right portion of the thoracic cavity. A light source (not shown) is also provided on endoscope 25 to illuminate the thoracic cavity. A video camera 26 is mounted to the proximal end of endoscope 25, and is connected to a video monitor 28 for viewing the interior of the thoracic cavity. A first suture organizing ring 30 is mounted to a proximal end of access cannula 22. A second organizing ring 32 is mounted to a support stand 34 fixed to table T. A replacement valve 36 is held at the distal end of an introducer 38 between first organizing ring 30 and second organizing ring 32. Introducer 38 extends through second organizing ring 32 and is supported by support stand 34. Additional instruments to be used in a procedure such as a retractor 40, as well as cutting, suturing, stapling, aspirating, irrigating and other devices, may be introduced through access cannula 22, trocar sleeves 24, and/or small, percutaneous incisions within intercostal spaces of the rib cage.

Figure 2:
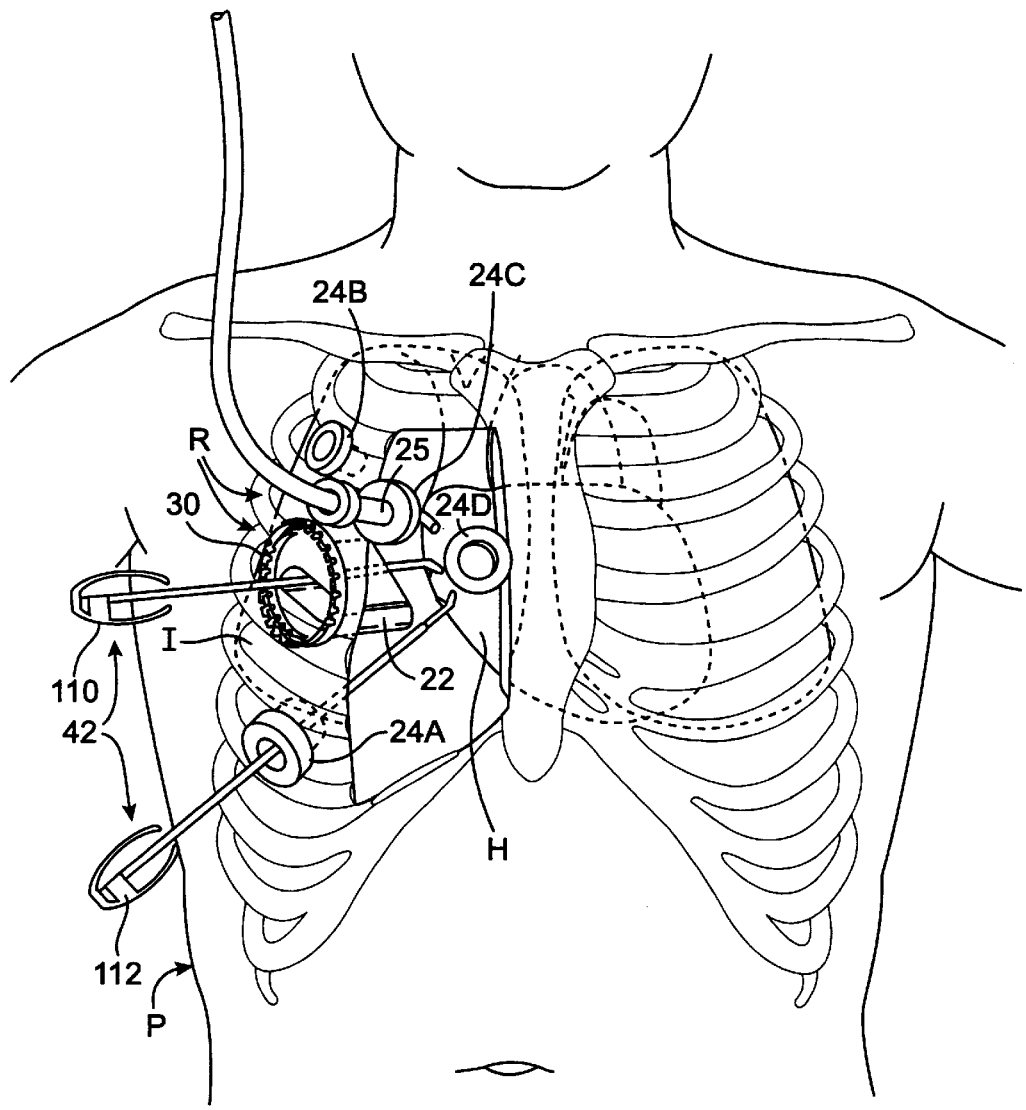
FIG. 2 is a front view of the procedure of FIG. 1, showing the positioning of the surgical instruments in the patient's chest.

Referring now to FIG. 2, access cannula 22 is positioned within an intercostal space I in the right lateral side of the chest, preferably in the third, fourth, fifth, or sixth intercostal space between adjacent ribs R. Additional trocar sleeves 24A, 24B are positioned within intercostal spaces superior and inferior to access cannula 22 in the right lateral side of the chest. Access cannula 22 and trocar sleeves 24A, 24B are positioned so that instruments 42 introduced through them may be directed toward the right side of the left atrium of the heart H. A trocar sleeve 24C is positioned in an intercostal space in the right anterior side of the chest such that endoscope 25 may be introduced to view the thoracic cavity and heart H without interfering with instruments introduced through access cannula 22 or trocar sleeves 24A, 24B. An additional trocar sleeve 24D is positioned in an intercostal space in the anterior side of the chest just to the right of the sternum and anterior to the right lateral side of the heart H.

It will be understood to those of ordinary skill in the art that, in some cases, it may desirable to eliminate some or all of trocar sleeves 24 and/or access cannula 22, and introduce instruments directly through small, percutaneous incisions in the chest. Advantageously, unlike laparoscopic, arthroscopic, and other endoscopic procedures, no distension of the chest is required using the method of the invention, so that leakage of distension fluid through percutaneous penetrations is not of concern. Thus, either thoracoscopic trocar sleeves without fluid seals or percutaneous incisions may be utilized for instrument introduction into the thoracic cavity. Trocar sleeves are generally preferred, however, in order to provide an open passage into the thoracic cavity, to protect adjacent tissue from injury resulting from contact with instruments, and to avoid damaging instruments, endoscopes, replacement valves, and the like when introduced into the thoracic cavity.

Referring again to FIG. 2, once access cannula 22 and trocar sleeves 24 have been positioned in the patient's chest, endoscope 25 is introduced through trocar sleeve 24D and camera 26 is connected to video monitor 28 (FIG. 1). Endoscope 25 is manipulated so as to provide a view of the right side of the heart, and particularly, a right side view of the left atrium. Usually, an endoscope of the type having an articulated distal end, or a distal end disposed at an angle between 30° and 90° will be used, which is commercially available from, for example, Olympus Corp., Medical Instruments Division, Lake Success, N.Y.

At this point in the procedure, if not previously accomplished, the patient is placed on cardiopulmonary bypass (CPB), the patient's right lung is at least partially collapsed, and the patient's heart is arrested. Suitable techniques for arresting cardiac function and establishing CPB without a thoracotomy are described in commonly-assigned, co-pending applications Ser. No. 07/991,188, filed Dec. 15, 1992, and Ser. No. 08/123,411, filed Sep. 17, 1993 (Attorney Docket No. 14635-4/93002-1), both of which are incorporated herein by reference.

Figure 3:
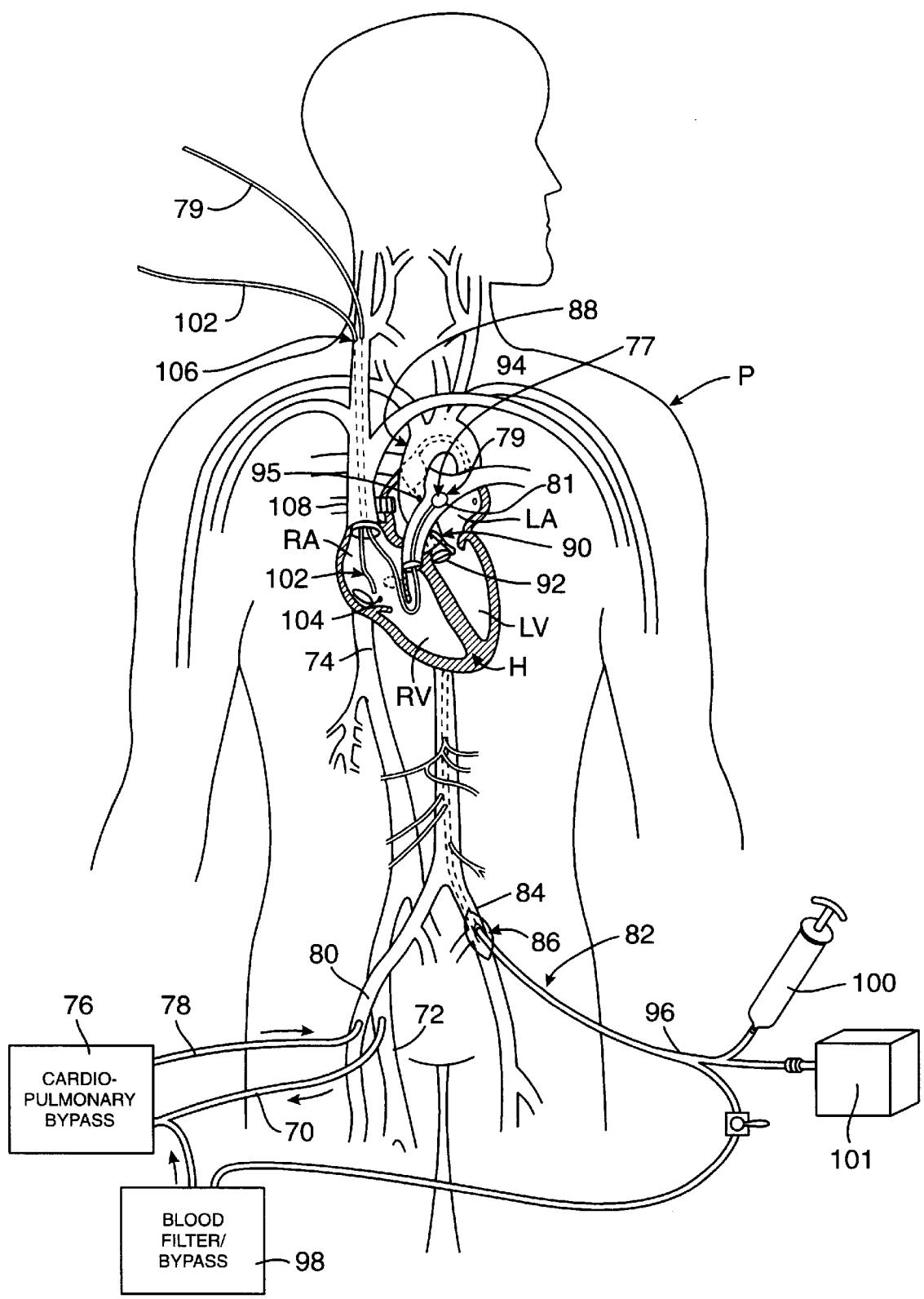
FIG. 3 is a front view of a patient's cardiovascular system illustrating the positioning of a system for arresting the heart and establishing cardiopulmonary bypass in accordance with closed-chest mitral valve replacement.

As illustrated in FIG. 3, CPB is established by introducing a venous cannula 70 into a femoral vein 72 in patient P and advancing venous cannula 72 into the inferior vena cava 74 and/or into the interior of heart H to withdraw deoxygenated blood therefrom. Venous cannula 70 is connected to a cardiopulmonary bypass system 76 which receives the withdrawn blood, oxygenates the blood, and returns the oxygenated blood to an arterial return cannula 78 positioned in a femoral artery 80. The right lung may also be collapsed at this time and cardiac function arrested using known techniques. Usually, a tube is introduced through the trachea into the right main stem bronchus, and a vacuum is applied through the tube to collapse the lung. Suitable methods for performing the above procedures may be found in commonly assigned, co-pending application Ser. No. 08/577,547, filed Dec. 22, 1995 (Attorney Docket No. 14635-002810), the complete disclosure of which has been previously incorporated herein by reference.

With cardiopulmonary bypass established, cardiac function arrested, and the right lung collapsed, the patient is prepared for surgical intervention within the heart H. Referring again to FIG. 2, a surgical cutting instrument such as angled scissors 110, as well as a grasping instrument such as grasping forceps 112, are introduced through access cannula 22 or through trocar sleeves 24A, 24B. Angled scissors 110 and forceps 112 are used to form an opening in the pericardium, providing access to the right side of the left atrium.

Figure 4A:
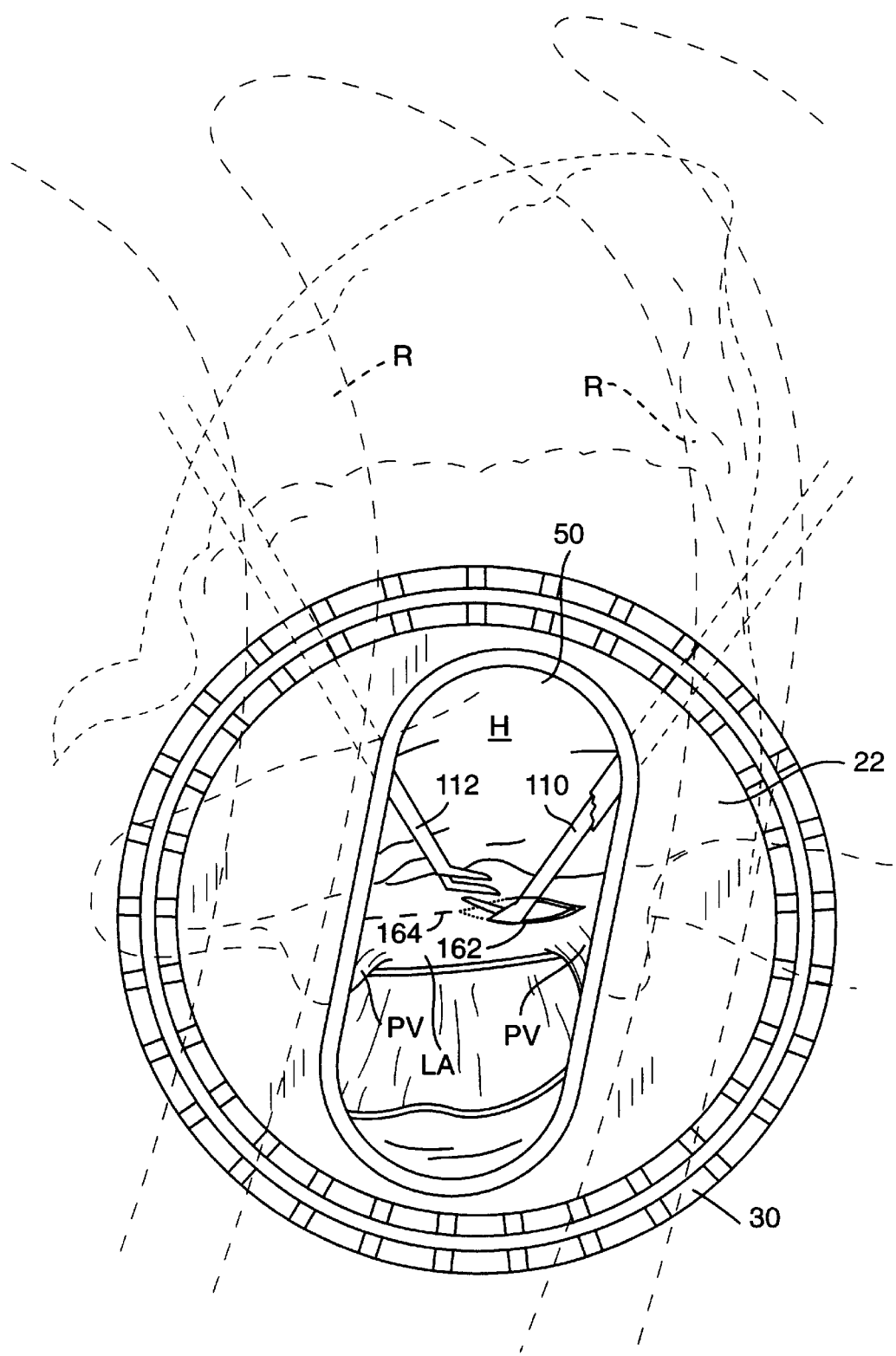
FIG. 4A is a top view looking into the patient's thoracic cavity through a passage of an access cannula in the system of FIG. 1, showing the creation of an atriotomy in the patient's left atrium.

FIG. 4A illustrates the view into the thoracic cavity through passage 50 of access cannula 22. Angled scissors 110 aided by grasping forceps 112 are shown cutting through the right side of left atrium LA to form an atriotomy 162. Atriotomy 162 is formed along dotted line 164 anterior to right pulmonary veins PV. A completed description of techniques for forming such an atriotomy is found in Kirklin and Barratt-Boyes, *Cardiac Surgery*, pp. 329–340, the disclosure of which has been incorporated herein by reference. Usually, atriotomy 162 will be formed under visualization by means of endoscope 25 (FIGS. 1 and 2), although direct viewing is possible through passage 50 of access cannula 22, or through a trocar sleeve 24.

Upon completion of atriotomy 162, the wall of left atrium LA on the anterior side of atriotomy 162 is retracted anteriorly by means of thoracoscopic retractor 40, as illustrated in FIG. 1. A variety of retractors 40 may be used and details on a suitable retractor for use with the present invention may be found in commonly assigned, co-pending application Ser. No. 08/577,547, filed Dec. 22, 1995 (Attorney Docket No. 14635-002810), the complete disclosure of which has been previously incorporated herein by reference. Retractor 40 is pulled in the anterior direction to retract the wall of left atrium LA, opening atriotomy 162 and exposing the patient's mitral valve MV within the left atrium LA.

Figure 4B:
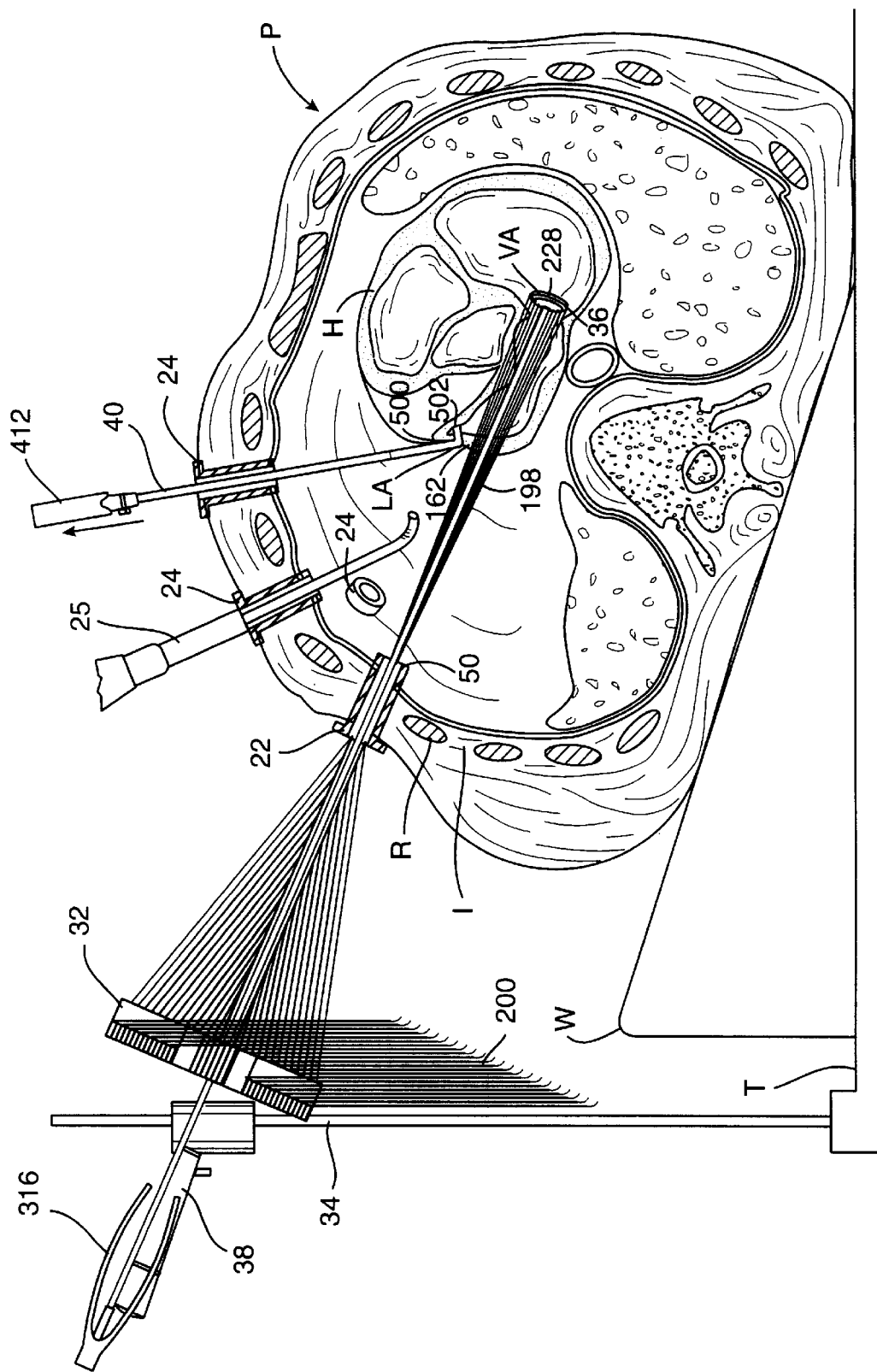
FIG. 4B is a transverse cross-sectional view of the patient of FIG. 1 taken through the patient's thorax, showing the introduction of the replacement valve into the left atrium and the tying of knots in the sutures to secure a prosthesis in the patient's heart.

Referring to FIG. 4B, retractor 40 is positioned so that tissue supporting member 500 is oriented with contact surface 502 extending towards the atriotomy in the left atrium LA. The surgeon then manipulates handle 412 to position tissue supporting member 500 in the atriotomy 162 so that the outer atrium wall AW is on contact surface 502. Once tissue supporting member 500 is in the desired position, the surgeon pulls retractor 40 proximally to retract atrium wall AW anteriorly, as shown in FIG. 4B. Tissue supporting member 500 preferably extends deeply into the left atrium LA so that the interatrial septum S is effectively supported on contact surface 502.

At this point, with atriotomy 162 retracted open, the mitral valve MV is exposed for an approach from the right lateral side of the chest via access cannula 22. Instruments may be introduced into the interior of the heart H through access cannula 22 or trocar sleeves 24. The instruments may extend through the atriotomy 162 to perform a procedure within the left atrium LA or may alternatively extend further through the mitral valve MV to gain access to the aortic valve in the left ventricle.

Replacement of the mitral valve MV typically comprises cutting or removal of all or part of the mitral valve leaflets VL. Once the valve leaflets are removed or reduced, it is usually necessary to size the valve annula VA so as to select a replacement valve 36 of proper size for patient P. Various methods and devices may be used for sizing the valve for replacement. As shown more clearly in FIG. 4B, with the correct valve selected, the replacement valve 36 is introduced into the left atrium and sutured to an annulus at the natural valve position in the heart. Replacement valve 36 may then be introduced into the left atrium LA by advancing introducer 38 through passage 50 of access cannula 22. Replacement valve 36 is oriented on introducer 38 so as to be introduced edge-first through passage 50. As replacement valve 36 is advanced into the thoracic cavity, organizing ring 32 maintains tension on sutures 198, allowing replacement valve 36 to slide along sutures 198. Introducer 38 is advanced through atriotomy 162 so that replacement valve 36 is disposed within left atrium LA. Replacement valve 36 is positioned against or within valve annulus VA. Square or overhand knots are then formed in sutures 198 outside of the patient's thoracic cavity, and the knots are pushed by a knot pusher 316 through passage 50 and atriotomy 162 toward sewing ring 228 of replacement valve 36. Suitable procedures for repair or replacement of the mitral valve may be found in commonly assigned, co-pending application Serial No. 08/577,547, filed Dec. 22, 1995 (Attorney Docket No. 14635-002810), the complete disclosure of which has been previously incorporated herein by reference.

After the mitral valve MV has been repaired or replaced, the above method is reversed to remove tissue supporting member 500 from the patient's thoracic cavity. The atrium wall AW is disengaged from contact surface 502 and tissue supporting member 500 is removed from the atriotomy. After atriotomy 162 has been closed, any remaining instruments are removed from the thoracic cavity. A chest tube may be introduced through one of the trocar sleeves 24 to facilitate evacuation of the pleural cavity. Access cannula 22 and trocar sleeves 24 are then removed from the chest wall, and the incisions or penetrations through which they were introduced are closed, usually by suturing or stapling.

The patient's lung may then be reinflated, and cardiac function may be restarted. As described in co-pending application Ser. No. 07/991,188, which has been incorporated herein by reference, infusion of cardioplegic fluid through aortic occlusion catheter 82 and/or retroperfusion catheter 102 is discontinued, and a saline solution is infused through one or both of these catheters to irrigate the heart and coronary arteries (see FIG. 3). The saline solution, along with blood, other fluids, air, thrombus, and other emboli within the heart or coronary arteries are then aspirated through the inner lumen of aortic occlusion catheter 82, as well as through venous cannula 70 and/or pulmonary venting catheter 79. Occlusion balloon 88 on aortic occlusion catheter 82 is then deflated, allowing warm, oxygenated blood to flow into the coronary arteries to perfuse the myocardium. Cardiac contractions will usually begin soon thereafter. In some cases, electrical defibrillation may be necessary to help restore cardiac function. Aortic occlusion catheter 82 and retroperfusion catheter 102 may then be removed from the patient. Cardiopulmonary bypass is then discontinued, and arterial cannula 78, venous cannula 70, and pulmonary venting catheter 79 are removed from the patient.

The above description is mainly for illustrative purposes, and other surgical procedures such as repair and replacement of aortic, tricuspid, or pulmonary valves, repair of atrial and ventricular septal defects, or the like may be employed with the present invention discussed below.

III. Tool Support Apparatus

Referring now to FIGS. 5–10, a surgical tool support apparatus of the present invention for use with a retractor 40, as mentioned above, will now be described. Although the tissue support apparatus 200 is described in the context of a mitral valve replacement procedure, it should be understood that the surgical tool support apparatus 200 may be used with a variety of other surgical interventional procedures performed in the thoracic cavity. During a typical mitral valve replacement procedure, cardiac tissue in the area of the left atrium may need to be retracted anteriorly to expose the mitral valve for a period of between about 30–90 minutes, typically between about 45–60 minutes. During this time period, it is desirable that the retractor 40 pull only in the anterior direction and not a combination of an anterior and lateral retraction. The position of retractor 40 during the period of anterior retraction should be maintained in a relatively constant manner so as to brace heart wall and cardiac tissue to provide a clear line of sight and access during this surgical procedure. As may occur during the course of mitral valve replacement, it may become necessary to remove the retractor 40 from the thoracic cavity to perform fluoroscopy or other surgical procedures which may require unobstructed access to the thoracic cavity or use of the trocar (puncture) occupied by the retractor 40.

Conventionally, retraction of the left atrium LA in an anterior fashion has been performed by an surgical assistant or scrub nurse who physically holds the retractor in the desired position for the duration of the valve replacement procedure or a portion thereof. Alternatively, it has been observed that surgeons use clamps or other collar mechanisms to implement a rudimentary locking device to prevent the shaft of the retractor 40 from moving in the distal direction during the operation. The present invention assists the cardiothoracic surgeon by providing an apparatus that replaces rudimentary locking devices used in a jerry-rigged or stop-gap fashion, while providing an easily removable and atraumatic positioning device for the retractor. The present invention has a compact configuration that will not further clutter the area of the surgical procedure. The invention also provides cost efficiencies arising from reduced manufacturing and material costs associated with its compact configuration.

Figure 5A:
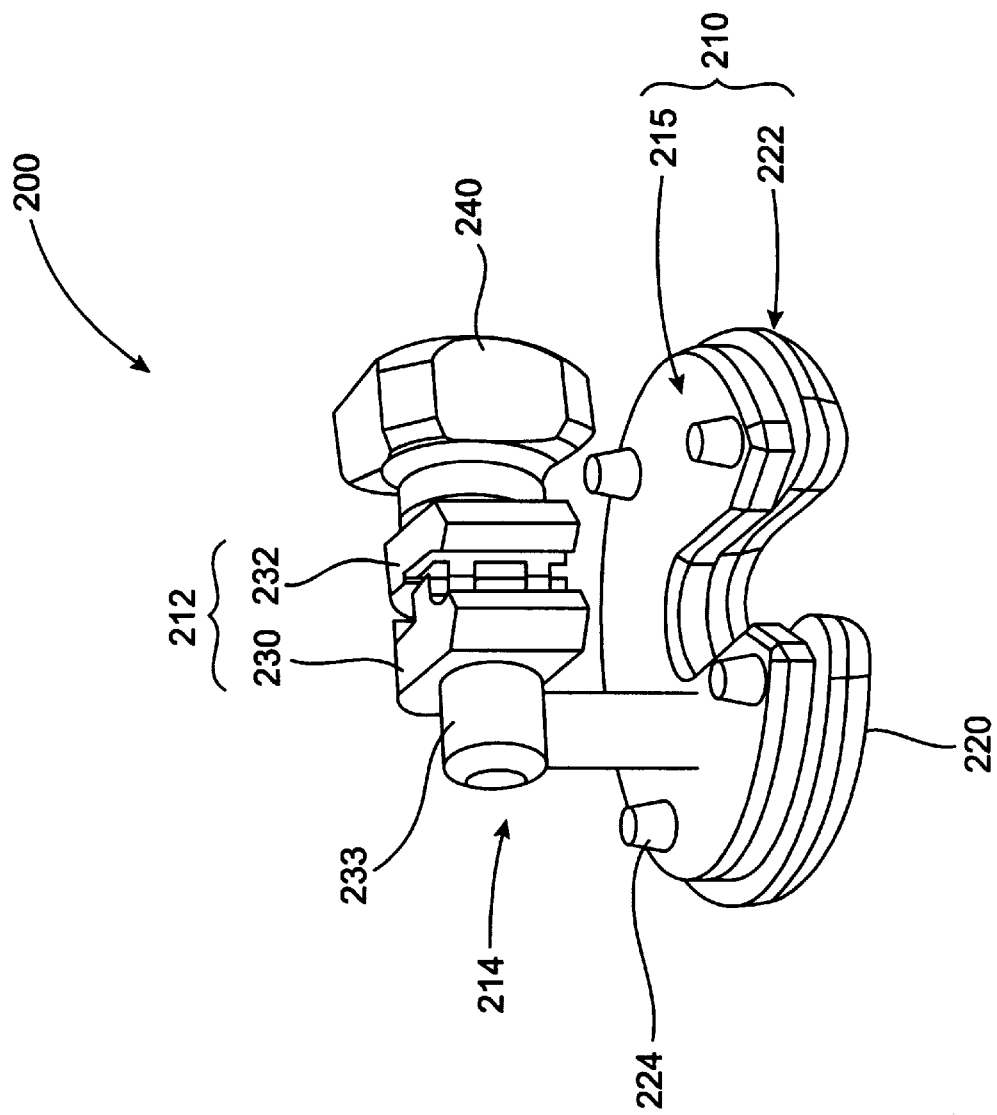
FIG. 5A is a perspective view of the support apparatus constructed in accordance with the principals of the present invention.
Figure 5C:
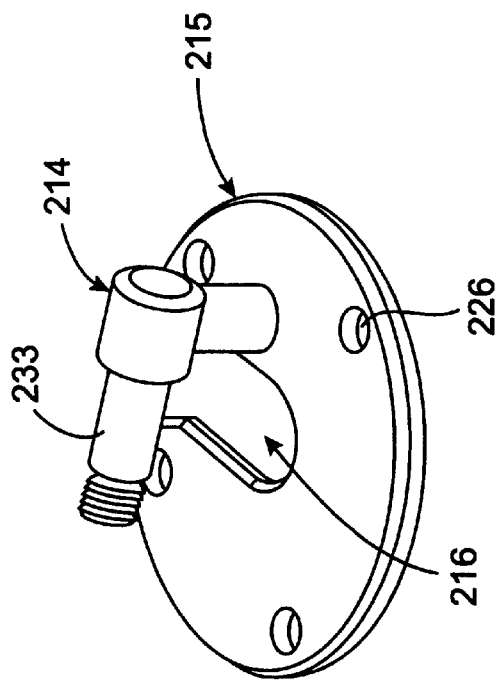
FIG. 5C is a perspective view of the base and L-shaped arm of the apparatus of FIG. 5A.

Referring to FIG. 5A, a preferred embodiment of the surgical tool support apparatus 200 comprises a base 210 and a clamp assembly 212 removably coupled to the base 210 by an L-shaped arm 214 (FIG. 5C). Arm 214, of course, may be of other configurations as necessary to properly position clamp assembly 212. Alternatively, the assembly 212 may be rotatably attached to the base 210 without the use of an arm 214. As shown, the base 210 typically comprises a rigid plate 215 formed from a non-corrosive, surgically compatible material such as surgical-grade stainless steel (303 stainless steel) or aluminum. The material should be able to withstand autoclaving and other types of sterilizing procedures so that the tool support apparatus 200 may be cleaned and reused. All parts on the apparatus 200 may also be disassembled to facilitate sterilization.

Figure 5B:
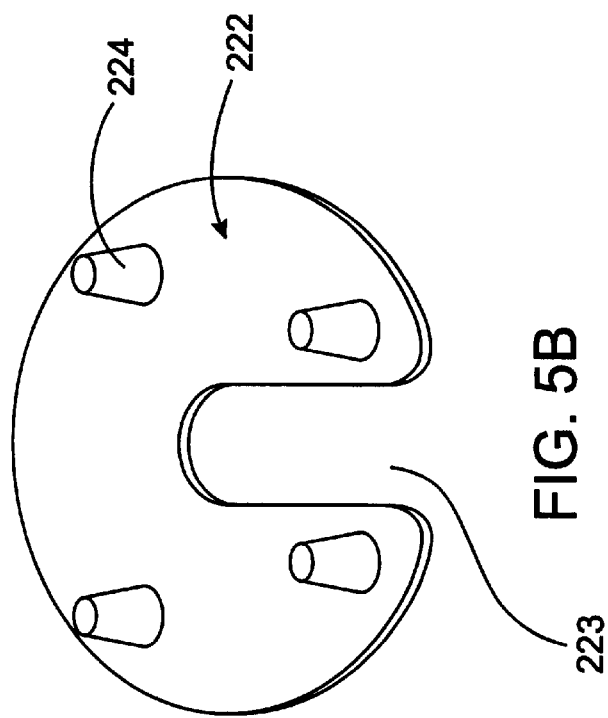
FIG. 5B is a perspective view of the cushion of the apparatus of FIG. 5A.

As shown more clearly in FIG. 5B–5C, the base 210 has an aperture 216 for receiving a shaft of the retractor 40. The aperture 216 facilitates engagement and alignment of clamps assembly 212 with the shaft of the retractor 40, and it should be understood that the aperture 216 may be a circular or closed path opening in the base or a slit, notch-like opening extending to an outer edge of the base 210 as shown in FIG. 5A.

Referring to FIGS. 5A–5B, the base 210 of the present invention has an atraumatic tissue-engaging surface 220. The surface 220 may be located directly on rigid plate 215. Preferably, base 210 comprises the rigid plate 215 and a biocompatible elastomeric cushion 222 coupled to the plate. The surface 220 would then be located on the cushion 222.

Cushion 222 has a cushion aperture 223 (FIG. 5B) corresponding to the aperture 216, and the cushion generally mirrors the outline of rigid plate 215. The maximum outer dimension of the tissue-engaging surface 220 is preferably no more than about 2 inches, more preferably no more than about 2.5 inches, and most preferably no more than about 3.5 inches. This maximum outer dimension is in reference to maximum outer diameter for disc-shaped surfaces or maximum horizontal width for surfaces of other configurations. The tissue-engaging surface 200 preferably has a surface area of at least about 3 square inches, more preferably at least 4 square inches, and most preferably at least 5 square inches. The tissue-engaging surface 220 of the support apparatus 200 lies on the surface of the patient's chest so that only the shaft passes into the patient's chest thereby minimizing trauma to the patient.

The elastomeric cushion 222 may be formed from a variety of materials such as 20 durometer silicone, with the understanding that the material will not agitate the area of the patient on which the tool support apparatus 200 rests. Preferably the elastomeric cushion 222 will also provide frictional resistance so as to provide a stable and relatively slip-resistant grip on the surface of the patient. The elastomeric cushion 222 may be integrally formed with the rigid plate 215 of the base 210, wherein the rigid plate provides structural support while the cushion 222 allows for the typically softer cushion 220. Alternatively, as shown in FIG. 5A, the elastomeric cushion 222 may have a plurality of protrusions 224 which frictionally engage a plurality of detents or through-holes 226 in the rigid plate of base 210 so that the cushion may be removably coupled to the rigid plate. It should be understood that other releasable engagement devices such as velcro or other detent/protrusion assemblies may be used to releasably couple the cushion 222 and the rigid plate 215.

In addition to being made preferably of biocompatible and frictional, high-traction material, the atraumatic tissue-engaging surface of the base 210 also has sufficient surface area so as not to induce a pressure sore or bruise on the patient while the retractor 40 and the tool support apparatus 200 are used. In retracting the left atrium LA during mitral valve MV replacement, the force encountered by the retractor 40 is between about 0.5 and 5 pounds, more typically between about 1–3 pounds. Pressures between about 0.5–1.0 psi, preferably about 0.98 psi, are desired and considered acceptable to provide atraumatic contact between the patient P and the apparatus 200 when a force of 3 pounds is applied normal to a surface of the patient for approximately one hour. It should be understood that a variety of different sized tissue-engaging surfaces 220 may be used depending on the amount of time and force applied during a particular interventional procedure. Referring to FIG. 5A, the area of the tissue-engaging surface 220 of the base 210 may be altered by using a variety of different sized elastomeric cushions 222 with the rigid plate 215 of the base 210. As noted above, the tissue-engaging surface 220 of the support apparatus 200 preferably has a surface area of at least about 3 square inches, more preferably at least 4 square inches, and most preferably at least 5 square inches.

Figure 6E:
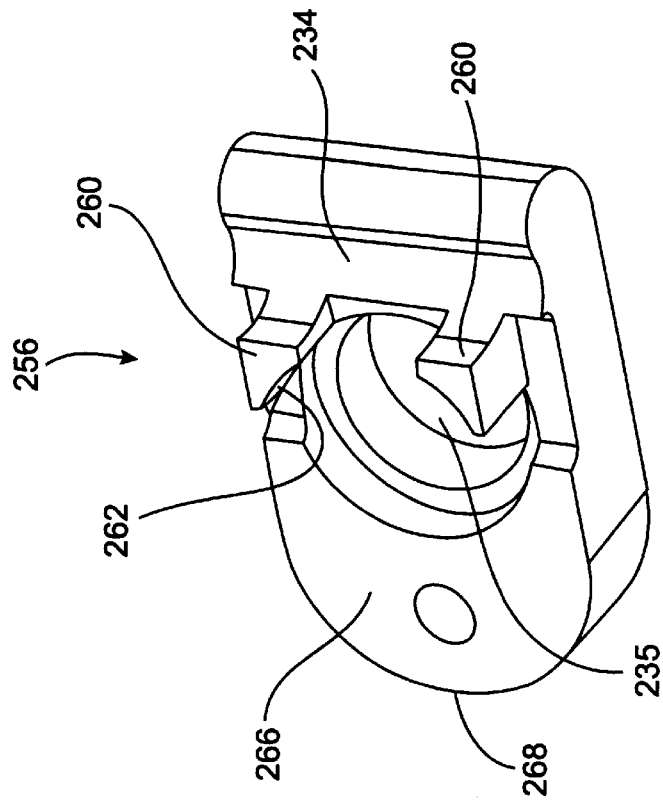
FIGS. 6D–6E are perspective views of the jaws used in the clamp assembly of the apparatus of FIG. 5A.
Figure 6D:
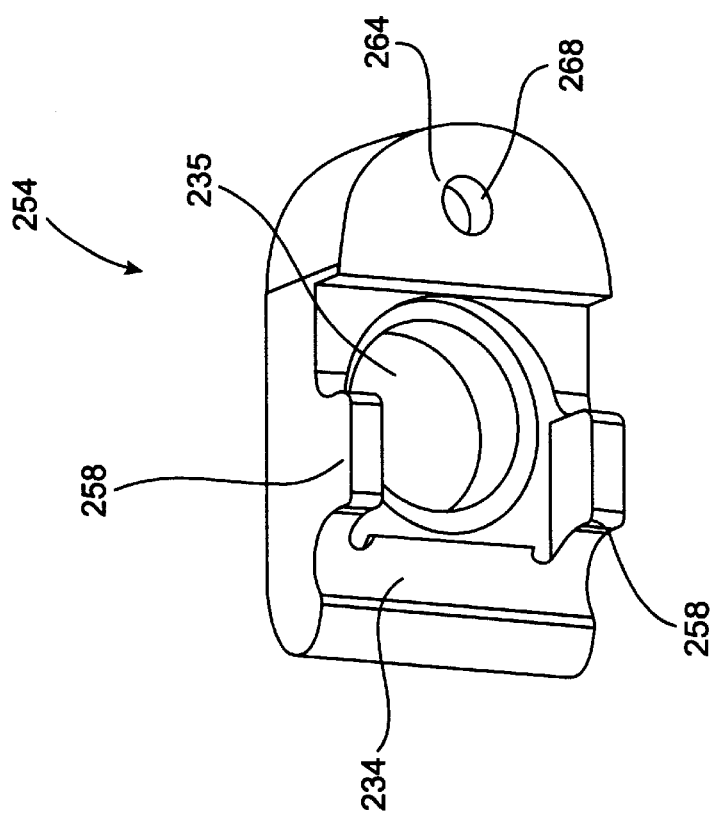

In a preferred embodiment, clamp assembly 212, as shown in FIGS. 5A and 6A, comprises a first jaw 230 and a second jaw 232. The pair of jaws are typically opposed to one another and are typically rotatably mounted on a segment 233 of L-shaped arm 214 generally parallel to the base 210. Clamp aperture 235 (FIG. 6D and 6E) and segment 233 act as a rotational linkage. This rotatability allows the clamp assembly 212 to engage the retractor 40 at a plurality of angles from which the retractor may extend from the body cavity (FIG. 7B). It should be understood that a variety of other devices known in the art may be used to rotatably couple the clamp assembly 212 to the arm 214.

Both the first jaw 230 and second jaw 232 have a retractor or tool engaging surface 234. The opposing jaws, in addition to being rotatable, are also axially translatable on the segment 233. A spring 236 such as a coil spring keeps the jaws apart when the clamp assembly is not engaging retractor 40. An axial translation limiter 238 coupled to the clamp assembly, such as a set screw, allows slidable axial translation but prevents the complete disengagement of the jaws 230 and 232 from the spring 236. The limiter 238 facilitates alignment between the jaws 230 and 232 so that they mate accurately. The spring 236 facilitates engagement of clamp assembly 212 with the retractor 40 by keeping the jaws apart prior to closing of the clamp assembly. It should be understood that a variety of different clamp assemblies may be used so long as the retractor can be releasably engaged and rotate about an axis typically parallel to the rigid plate of the base 210.

A variety of different closure devices may be used to close and engage the clamp assembly 212 with the retractor 40. FIGS. 5A and 6A show a thumb-screw 240 threaded on the horizontal rod or segment 233 (FIG. 5C) of arm 214. Alternatively, a cam-release device 250 as shown in FIGS. 6B and 6C maybe pivotally attached to distal end of generally horizontal segment of arm 214 to provide closing of the jaws 230 and 232.

As shown more clearly in FIGS. 6C, each jaw 230 and 232 of the clamp assembly 212 has a protrusion 252 to facilitate alignment of the jaws 230 and 232 when the clamp assembly is closed. Both the protrusions 252 are typically machined into the inside, opposing faces of the jaws 230 and 232. An exemplary embodiment of jaws of the clamp assembly 212 are shown in FIGS. 6D and 6E. First integrated jaw 254 and second integrated jaw 256 have protrusions 258 and 260 formed with the jaws for facilitating alignment during closure of the assembly 212. First, outer protrusions 258 fit over the second, inner protrusions 260 when the jaws are engaged. Second, inner protrusions 260 have a surface 262 which generally conforms with the horizontal, preferably rod-shaped segment 233 of the arm 214 to facilitate sliding translation of the second jaw 256.

Overtightening surfaces 264 and 266 on the jaws 254 and 256 prevent complete closure of retractor engagement surfaces 234 which may damage the retractor 40. Alternatively, retractor engagement surface 234 may be coated with an elastomeric material such as silicone to improve frictional contact between the retractor and the clamp assembly 212. The covering (not shown) may also prevent crimping damage which would likely result if the clamp assembly 212 is overtightened on the retractor 40. Holes 268 on surfaces 264 and 266 are provided for engaging the set screw 238.

Figure 7A:
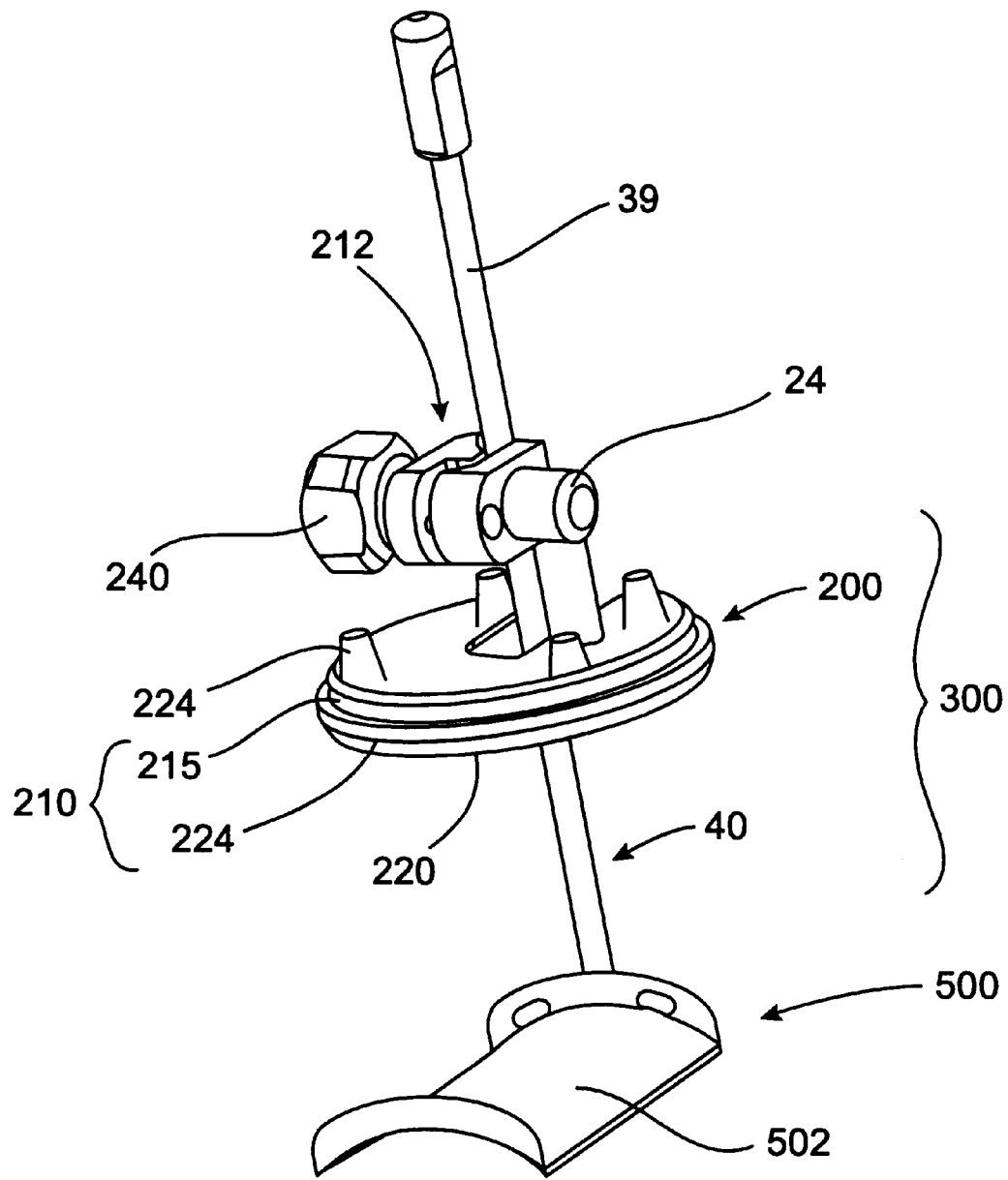
FIG. 7A is a perspective view of the system of the present invention.
Figure 7B:
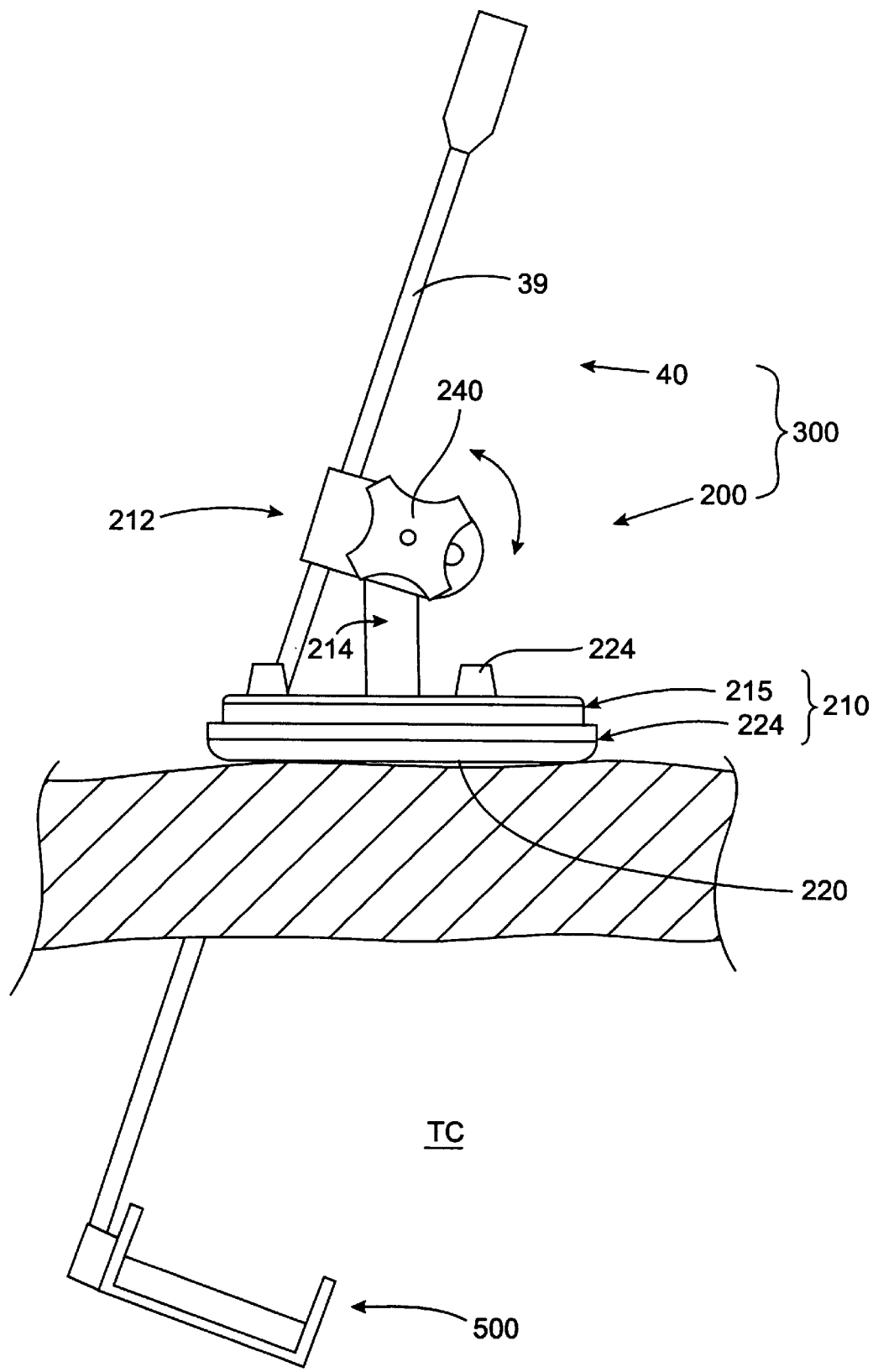
FIG. 7B is cross-sectional view of a portion of the thoracic cavity with a retractor of the system of FIG. 7A exiting the cavity at a non-perpendicular angle and coupled to the support apparatus of the system.

Referring now to FIG. 7A, the system 300 for manipulating tissue structure in the thoracic cavity comprises a retractor 40 and the tool support apparatus 200. Once coupled to the apparatus 200, the shaft 39 of the retractor 40 acts as a linking member between the contact surface 502 on tissue supporting member 500 and the tissue-engaging surface 220. The surfaces 220 and 502 act like a clamp to reposition tissue in a body cavity while pressing against typically a outer surface of the patient or body cavity. Clamp assembly 212 on the apparatus 200 is used to secure the apparatus 220 to the retractor 40. It should be understood that although in the preferred embodiment the tool support apparatus 200 is removably coupled to the retractor 40, alternate embodiments of the system 300 may comprise a retractor 40 that may be slidably but undetachably coupled to the support apparatus 200.

Referring to FIG. 7B, the ability to rotate the clamp assembly 212 on segment 233 (FIGS. 5A and 5C) allows the apparatus 200 to engage shaft 39 of the retractor 40 when the shaft does not exit a body cavity, such as the thoracic cavity TC, at a normal angle. This aspect of the present invention allows support apparatus 200 to position the tissue support member 500 at a variety of angles to best provide access and line of sight to the area of surgical intervention.

Figure 8:
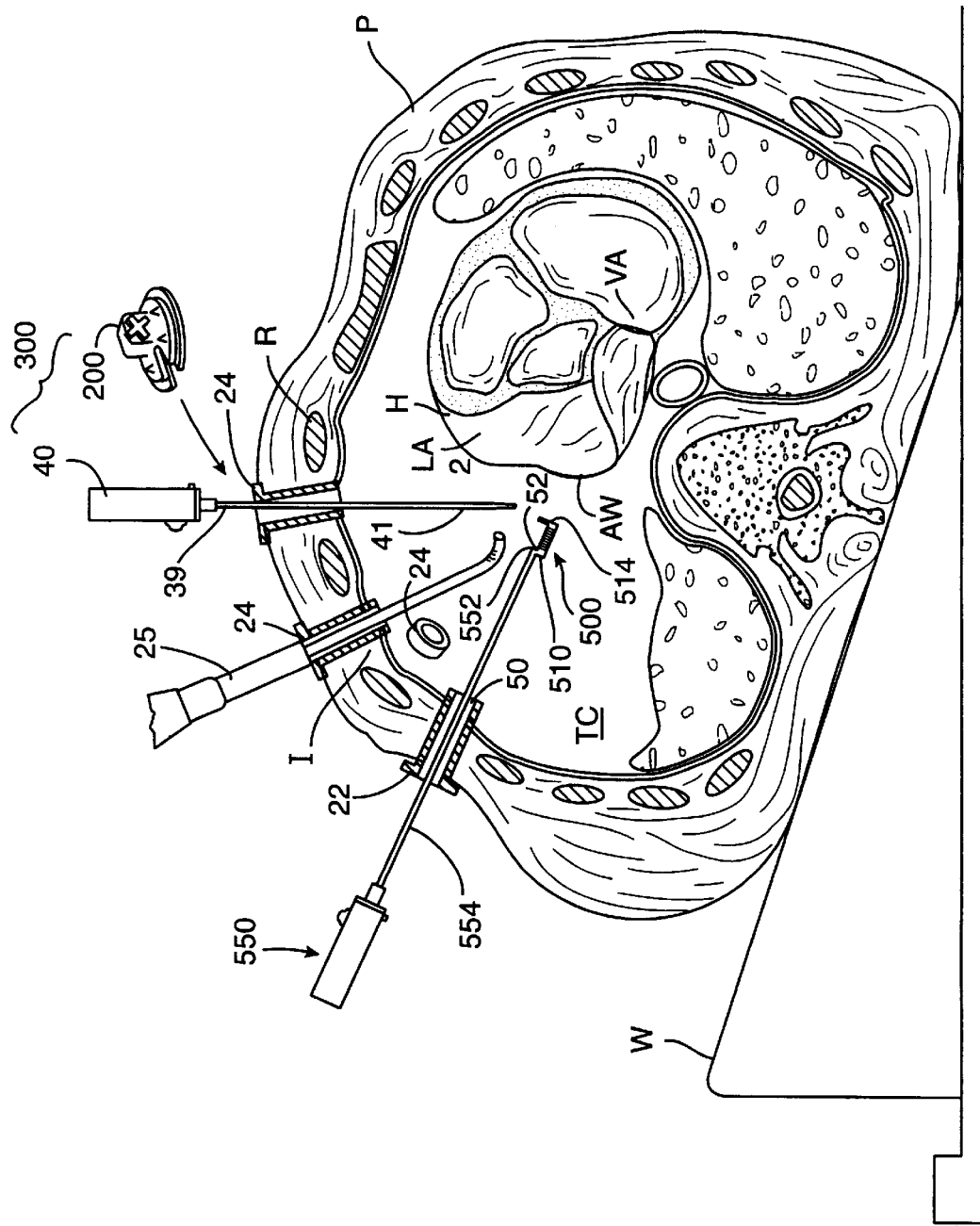
FIGS. 8–9 is a transverse cross-sectional view of the patient of FIG. 1 taken through the patient's thorax, showing the assembly of a retractor or tissue positioning tool and the use of the tool with a tool support apparatus.
Figure 9:
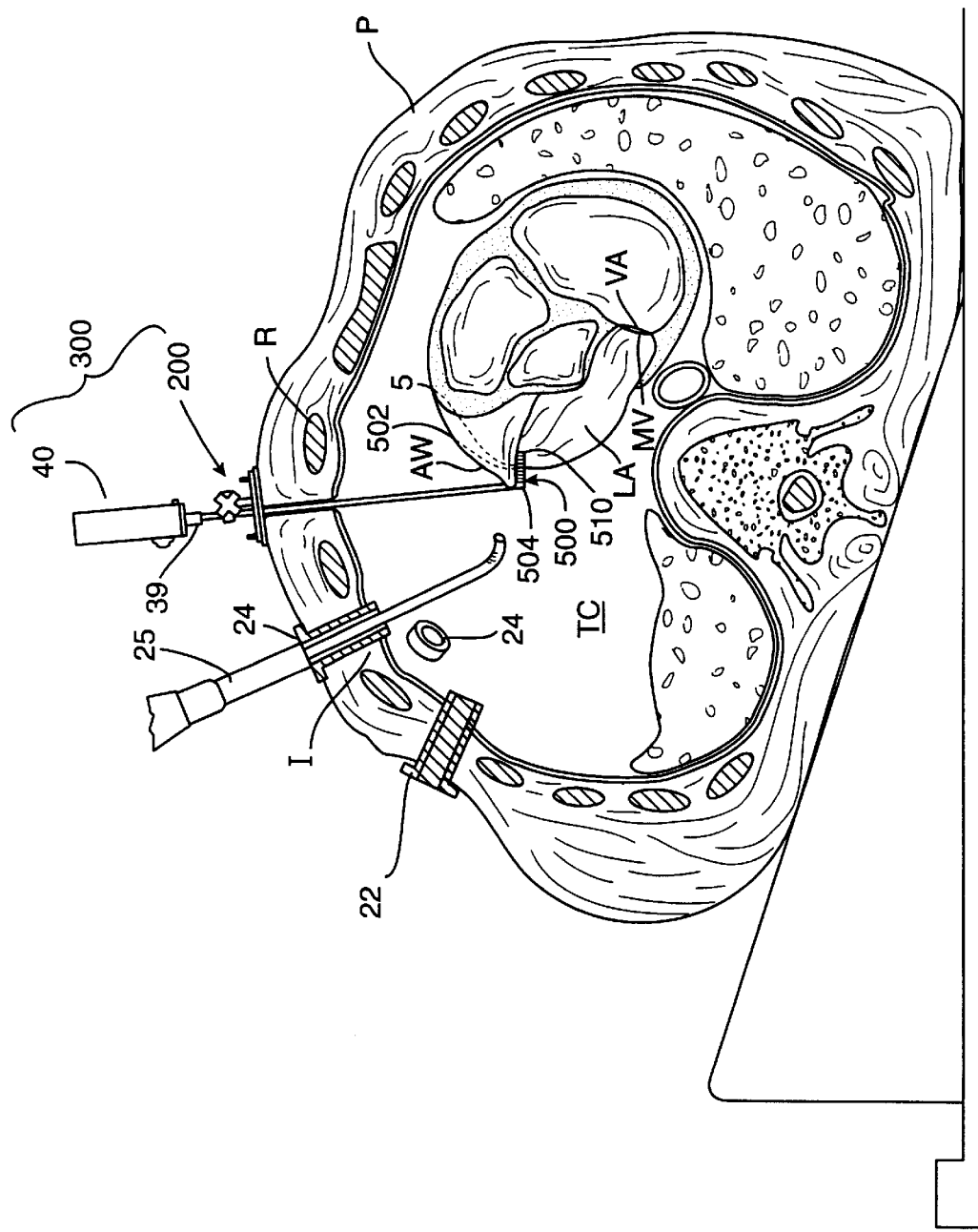
Figure 10:
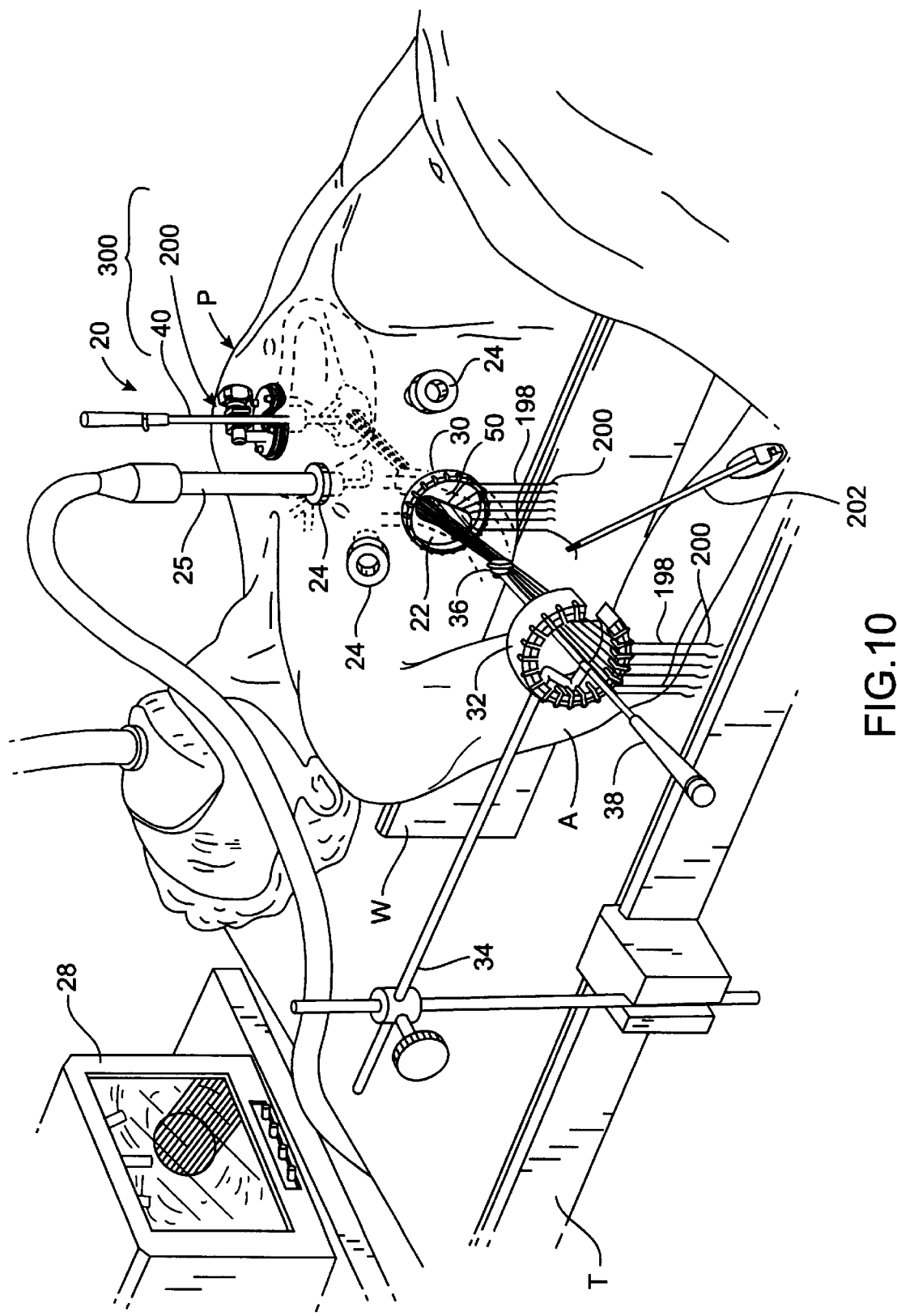
FIG. 10 is a perspective view of a closed-chest mitral valve replacement using minimally invasive techniques, a retractor, and a tool support apparatus of the present invention.

A method for manipulating tissue structure using system 300 will now be described with reference to FIGS. 8–10. The method comprises introducing a tissue positioning tool such as the retractor 40 having shaft 39 (FIG. 7A) within the thoracic cavity through a percutaneous penetration. The tool or retractor 40 may be assembled within the thoracic cavity TC as shown in FIG. 8. The tool may also be introduced through trocar 24 or alternatively through a percutaneous puncture without the trocar (FIG. 9). In certain scenarios, it is necessary to introduce individual portions of the tissue positioning tool 40 through first and second percutaneous penetrations in the thoracic cavity. FIG. 8 shows the retractor 40 inserted through trocar 24 while tissue supporting member 500 is inserted through trocar 22. The distal tip 41 of the retractor 40 may be threaded or otherwise adapted to be releasably coupled to the tissue supporting member 500. The retractor 40 is coupled to the member 500 and is now ready to engage the tissue surface (FIG. 9). It should be noted that the tool support apparatus 200 may be connected to shaft 39 of the retractor 40 either prior to inserting the retractor 40 into the trocar 24 or anytime thereafter.

With the tool or retractor 40 ready to engage the tissue structure such as the atrium wall AW of the left atrium LA, force is applied to the shaft of the tissue positioning tool to retract the tissue structure. FIG. 9 shows the system 300 where the tissue supporting member 500 and the retractor 40 have been introduced into the thoracic cavity and positioned to maintain a force against the tissue structure of the patient's heart. This force, typically between about 1–3 lbs, provides retraction that opens the line of sight and access to the mitral valve MV. Once the tool or retractor 40 is in position, the tool support apparatus 200 may be positioned or repositioned along the shaft 39. Adjustments are then made to engage or close the clamp assembly 212 on the support apparatus 200 with the shaft 39. This may involve tightening a thumb-screw, pulling on a release lever, or using other known methods of closure. By pressing against a surface of the patient such as the outer surface of the chest, the apparatus 200 can position the retractor 40 and maintain the retractive force on the retractor as required to provide line of sight and open access to the mitral valve MV. FIG. 9 shows an optional aspect of the method where the trocar 24 is not used with the retractor 40 through the percutaneous intercostal penetration. FIG. 10 provides an alternate view of the apparatus 200 engaged to the retractor 40 and resting on the chest of a patient. Although the drawings show the retractor 40 positioned at an angle normal to the surface of the patient, it should be understood that the apparatus 200 can engage and position the retractor 40 at a variety of other different angles.

Figure 11B:
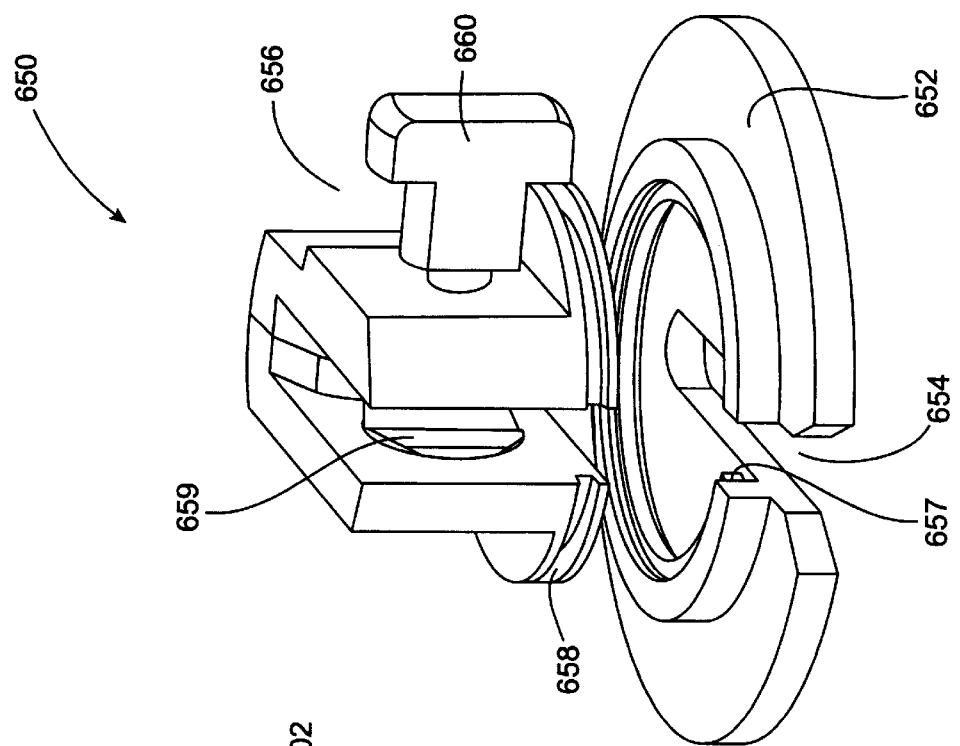
FIGS. 11A–11B are perspective views of alternate embodiments of a tool support apparatus of the present invention.
Figure 11A:
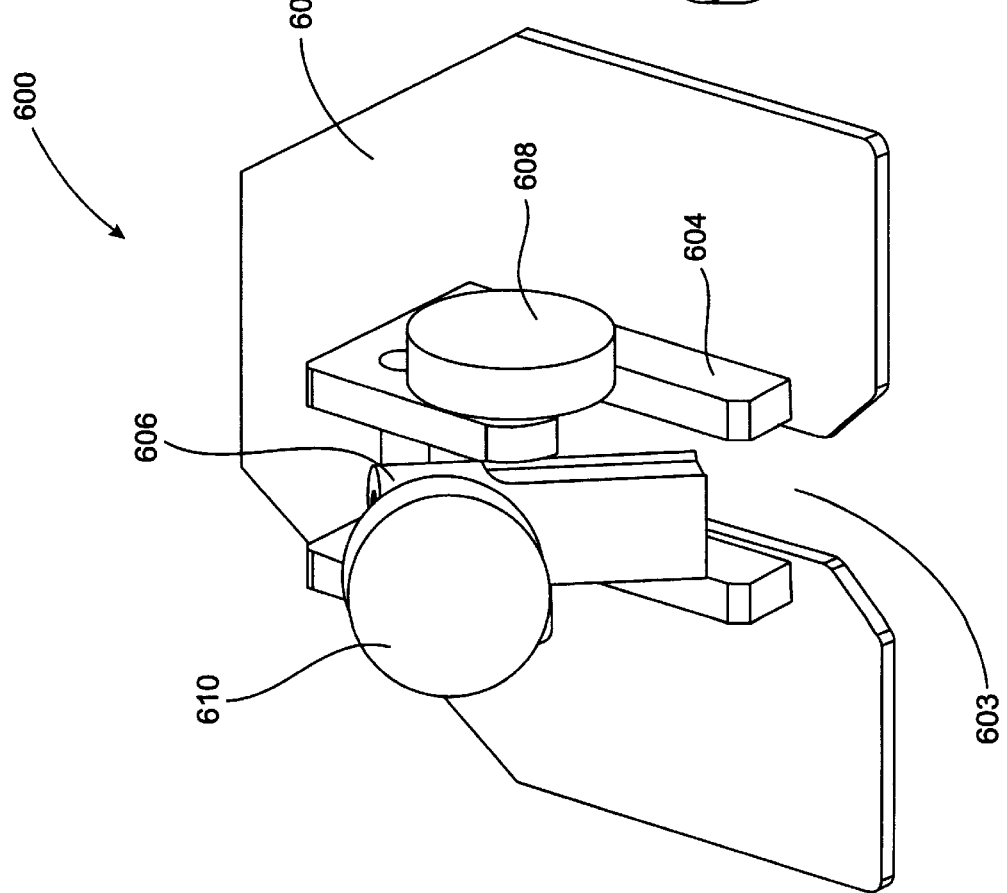

Referring now to FIGS. 11A and 11B, alterative embodiments of the tool support apparatus 200 will be described. In FIG. 11A, the first alternate support apparatus 600 comprises of a first alternate base 602 having an aperture 603 and a carriage 604 for rotatably supporting an engagement assembly 606 to base 602. A shaft (not shown) extending between the carriage 604 has a user interface 608 that provides rotational positioning for the engagement clamp assembly 606. A set screw 610 provides frictional engagement with a retractor 40.

FIG. 11B illustrates a second alternate support apparatus 650 which has a second alternate base 652 having an aperture 654. The base 652 is removably coupled to an engagement assembly 656 which is removably coupled to base 652. The base has a tongue 657 for releasably engaging groove 658 on engagement assembly 656. Engagement assembly 656 has an engagement surface 659 which is rotatable about an axis horizontally parallel to the base 652. A screw-type tightening device 660 can be used to engage a second, opposing engagement surface (not shown) against engagement surface 659 to hold a retractor 40 therebetween. The apparatus of the present invention may have a variety of different embodiments so long as the apparatus has a base of sufficient surface area to prevent trauma to the patient, an aperture or open space for accommodating the retractor 40, and a clamp assembly that can engage a tool and rotate about an axis generally horizontal to the base.

Figure 12:
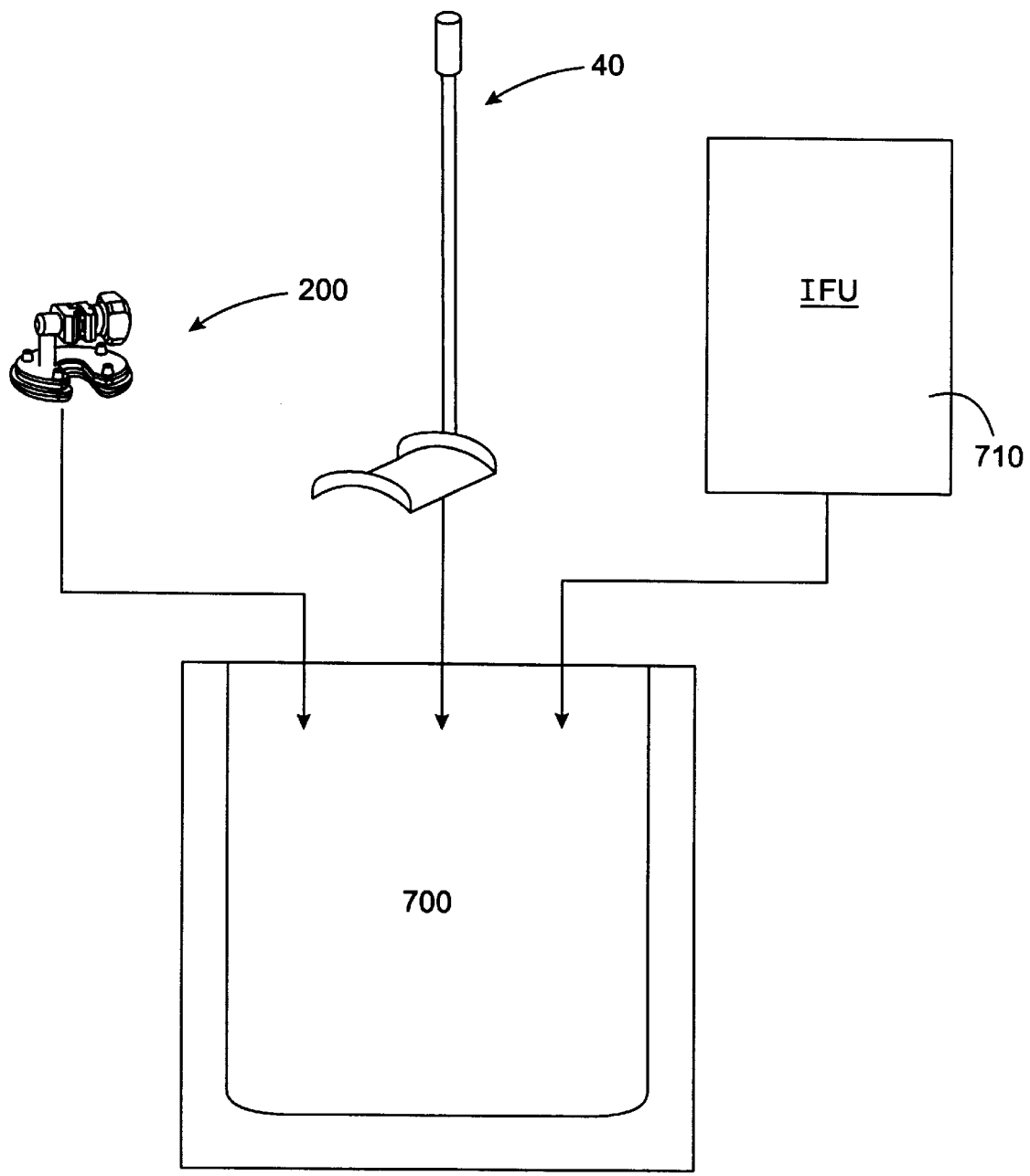
FIG. 12 shows a kit of the present invention containing a tissue positioning tool, a tool support apparatus of the present invention, and instructions for use in accordance with a method of the present invention.

A tool support apparatus 200 according to the present invention may be packaged together with instructions for use (IFU) in a kit as shown in FIG. 12. A conventional package, which may be a pouch 700 or any other suitable package, such as a tray, box, tube, or the like, may be used to contain the apparatus 200 and IFU 710, where the IFU may be printed on a separate sheet and/or may be printed on the packaging itself. The kit may also include a retractor 40 which may be permanently or releasably coupled to the apparatus 200. Optionally, but not necessarily, the tool support apparatus 200 and/or the retractor 40 may be sterilized within the package, e.g. by radiation or ethyleneoxide. The instructions will set forth any of the aspects of the method of the present invention described above.

Although the foregoing invention has been described in some detail by way of illustration and example, for purposes of clarity of understanding, it will be obvious that certain changes and modifications may be practiced within the scope of the appended claims.

What is claimed is:

1. A method for manipulating a tissue structure within a thoracic cavity of a patient, comprising the steps of:

providing a tissue positioning tool having a shaft, a tool support apparatus, and a tissue supporting member, the tool support apparatus having a clamp assembly configured to secure the shaft to the tool support apparatus, the tool support apparatus also having a base, the clamp assembly being pivotable relative to the base;

positioning the tool support apparatus on an outer surface of a patient's chest;

introducing the tissue supporting member into the patient's thoracic cavity;

contacting a tissue structure in the thoracic cavity with the tissue supporting member, the tissue supporting member being coupled to the shaft;

applying a force to the shaft so that the tissue supporting member moves the tissue structure to a displaced position; and locking the shaft to the tool support apparatus with the clamp assembly after the applying step so that the tissue structure maintains the displaced position.

2. The method of claim 1, wherein the providing step is carried out with the clamp assembly having an actuator, the actuator being movable to a locked position which secures the shaft relative to the tool support apparatus, the actuator also fixing an angular orientation of the clamp assembly relative to the base when moved to the locked position thereby preventing pivoting of the clamp assembly relative to the base.

3. The method of claim 1, wherein the locking, applying, contacting, introducing and positioning steps are carried out with only the shaft penetrating the patient's chest and the tool support apparatus engaging only the outer surface of the patient's chest.

4. The method of claim 1, wherein the providing step is carried out with the tool support apparatus having a base, the base having a bottom surface having a surface area of at least 3 square inches.

5. The method of claim 1, wherein:

the providing step is carried out with the tool support apparatus having an elastomeric cushion; and the positioning step is carried out with the elastomeric cushion engaging the outer surface of the patient's chest.

6. A method for manipulating a tissue structure within a thoracic cavity of a patient, comprising the steps of:

providing a tissue positioning tool having a shaft, a tool support apparatus, and a tissue supporting member, the tool support apparatus having a clamp assembly configured to secure the shaft to the tool support apparatus;

positioning the tool support apparatus on an outer surface of a patient's chest;

introducing the tissue supporting member into the patient's thoracic cavity;

contacting a tissue structure in the thoracic cavity with the tissue supporting member, the tissue supporting member being coupled to the shaft;

applying a force to the shaft so that the tissue supporting member moves the tissue structure to a displaced position; and locking the shaft to the tool support apparatus with the clamp assembly after the applying step so that the tissue structure maintains the displaced position;

the introducing step being carried out with the tissue supporting member passing through a first opening in the patient's chest; and the applying step being carried out with the shaft passing through a second opening in the patient's chest.

7. The method of claim 6, wherein the providing step is carried out with the tool support apparatus having a base, the clamp assembly being pivotable relative to the base.

8. The method of claim 6, further comprising the step of:

attaching the tissue supporting member to the shaft within the patient's chest.

9. A method for manipulating a tissue structure within a thoracic cavity of a patient, comprising the steps of:

providing a tissue positioning tool having a shaft, a tool support apparatus, and a tissue supporting member, the tool support apparatus having a clamp assembly configured to secure the shaft to the tool support apparatus, the tool support apparatus also having a base, the base having a bottom surface having a surface area of at least 3 square inches and a maximum outer dimension of no more than 3.5 inches;

positioning the tool support apparatus on an outer surface of a patient's chest;

introducing the tissue supporting member into the patient's thoracic cavity;

contacting a tissue structure in the thoracic cavity with the tissue supporting member, the tissue supporting member being coupled to the shaft;

applying a force to the shaft so that the tissue supporting member moves the tissue structure to a displaced position; and locking the shaft to the tool support apparatus with the clamp assembly after the applying step so that the tissue structure maintains the displaced position.

10. The method of claim 9, wherein the providing step is carried out with the bottom surface having a circular shape with a radial slot.

11. A method of retracting a tissue structure, comprising the steps of:

providing a tissue positioning tool having a shaft and a tissue supporting member;

introducing the tissue supporting member into the patient through a first penetration in the patient;

introducing the shaft through a second penetration in the patient;

attaching the tissue supporting member to the shaft within the patient;

contacting a tissue structure in the patient with the tissue supporting member; and applying a force to the shaft so that the tissue supporting member moves the tissue structure to a displaced position.

12. The method of claim 11, wherein the providing step is carried out with the tissue positioning tool including a tool support apparatus.

13. The method of claim 12, further comprising the steps of:

positioning the tool support apparatus on an outer surface of a patient's chest; and locking the shaft to the tool support apparatus after the applying step so that the tissue structure maintains the displaced position.

* * * * *